United States Patent [19]

Kondo et al.

[11] Patent Number: 5,028,601
[45] Date of Patent: Jul. 2, 1991

[54] CEPHALOSPORIN COMPOUNDS AND ANTIBACTERIAL AGENTS

[75] Inventors: Shinichi Kondo; Takashi Tsuruoka; Katsuyoshi Iwamatsu; Kiyoaki Katano; Satoru Nakabayashi; Hiroko Ogino; Takashi Yoshida; Masaji Sezaki, all of Yokohama, Japan

[73] Assignees: Meiji Saika Kaisha, Ltd.; Zaidanhojin Biseibutsu Kagaku Kenkyukai, both of Tokyo, Japan

[21] Appl. No.: 184,323

[22] Filed: Apr. 21, 1988

[30] Foreign Application Priority Data

Apr. 30, 1987 [JP] Japan .................. 62-108227

[51] Int. Cl.$^5$ .................. C07D 501/20; A61K 31/545
[52] U.S. Cl. .................. 514/206; 514/202; 514/209; 540/222; 540/225; 540/228
[58] Field of Search .............. 540/222, 227, 225, 228; 514/202, 206, 209

[56] References Cited

U.S. PATENT DOCUMENTS

| | | | |
|---|---|---|---|
| 4,758,557 | 7/1988 | Tsuruoka et al. | 514/206 |
| 4,822,786 | 4/1989 | Zama et al. | 540/225 |
| 4,971,961 | 11/1990 | Iwamatsu et al. | 540/225 |

FOREIGN PATENT DOCUMENTS

0251299 1/1988 European Pat. Off. .

*Primary Examiner*—Nicholas S. Rizzo
*Attorney, Agent, or Firm*—Jordan and Hamburg

[57] ABSTRACT

Cephalosporin compounds of the formula (I):

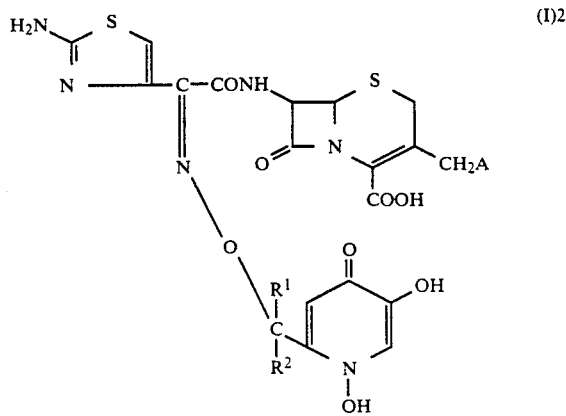

wherein $R^1$ and $R^2$ may be the same or different and are a hydrogen atom or a lower alkyl group of 1–5 carbon atoms and A is a hydrogen atom or a nucleophilic compound residue or pharmacologically acceptable salts thereof have excellent antibacterial activity against Gram positive and Gram negative microorganisms.

3 Claims, No Drawings

CEPHALOSPORIN COMPOUNDS AND ANTIBACTERIAL AGENTS

BACKGROUND OF THE INVENTION

1. Field of the Invention

This invention relates to cephalosporin compounds having antibacterial activity in a wide range including pseudomonas aeruginosa, and more specifically, it relates to cephalosporin derivatives having a (Z)-2-(2-aminothiazole-4-yl)-2-(1,5-dihydroxy-4-pyridone-2-yl) alkoxyiminoacetamido group on the 7-position which have an excellent therapeutic effect against diseases in humans and animals due to pathogens and are useful as medicines and veterinary medicines.

2. Description of the Prior Art

Cephalosporin antibiotics are widely employed in the treatment of diseases due to pathogenic bacteria, but are hardly satisfactory in view of antibacterial power, antibacterial spectrum, clinical pharmaceutical effect etc.

The present inventors had previously discovered that novel cephalosporin derivatives having a 2-(2-aminothiazole-4-yl)-2-(1,5-dihydroxy-4-pyridone -2-carboxamido)acetamido group on the 7-position have strong activity against a wide range of pathogens in Japanese Patent Application Nos. 60-140989, 61-77893 and 61-77894. These derivatives especially have excellent antibacterial power against Pseudomonas aeruginosa and it is believed that the activity is derived from the 1,5-dihydroxy-4-pyridone-2-carboxamido substituent on the 7-position, and further on this occasion, the study on the 1,5-dihydroxy-4-pyridone structure has been developed and the side-chains on the 7-position have been intensively studied, finally to discover that the novel cephalosporin compounds of the formula (I) have a wide range of antibacterial activity against Gram negative bacteria including Pseudomonas aeruginosa and also have particularly strong activity against various β-lactamase producing bacteria, whereby this invention has been accomplished.

SUMMARY OF THE INVENTION

Accordingly, this invention relates to novel cephalosporin compounds of the general formula (I):

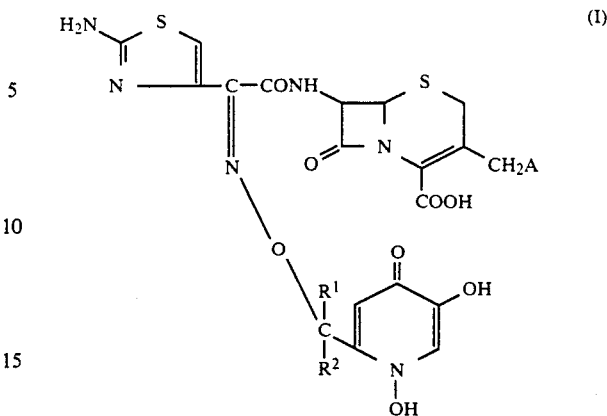

wherein $R^1$ and $R^2$ may be the same or different and are a hydrogen atom, a lower alkyl group of 1-5 carbon atoms, a phenyl group or a substituted phenyl group and A is a hydrogen atom or a nucleophilic compound residue, which are useful as antibacterial agents, pharmacologically acceptable salts thereof and antibacterial agents containing the same as the active ingredient.

DETAILED DESCRIPTION OF THE INVENTION

The compounds of the general formula (I) are synisomers, and where there is an asymmetric carbon in the substituent on the 7-position, D-form and L-form may be present, and this invention excompasses both of D- and L- forms and also DL-form. Further, the 1,5-dihydroxy-4-pyridine-2-alkoxyimino moiety as the substituent on the 7-position may exist as tautomers as described below, and although this invention encompasses both of these, the pyridone form is used for therterminology and the description of the structure.

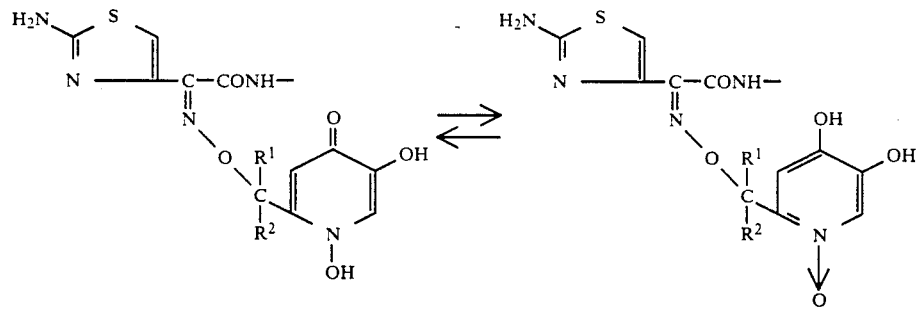

Examples of the pharmacologically acceptable salts of the compounds of the formula (I) of this invention include medicinally acceptable salts, in particular, conventionally employed non-toxic salts, for example, alkali metal salts such as sodium salts, potassium salts etc., alkaline earth metal salts such as calcium salts, magnesium salts etc., ammonium salts, organic salts such as those with organic bases, for example, organic amine salts such as triethylamine salts, pyridine salts, ethanolamine salts, triethanolamine salts, dicyclohexylamine salts, basic amino acid salts such as those with lysine, arginine etc.

Example of the nucleophilic compound residue represented by A in the compounds of the general formula (I) include a hydroxyl group, a mercapto group, a carbamoyl group, a carbamoyloxy group, an azido group, an alkanoyloxy group of 2-5 carbon atoms or a quaternary ammonium group such as a pyridinium or substituted pyridinium group of the formula:

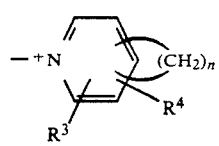

wherein n is 0 or an integer of 3-5 and $R^3$ and $R^4$ may be the same or different and are a hydrogen atom, a halogen atom, a straight-chain or branched-chain alkyl group of 1-5 carbon atoms, a hydroxyl group, an amino group, a carbamoyl group, a sulfonic acid group, a sulfonamido group, a sulfoalkyl group, a straight-chain or branched-chain alkylthio group of 1-5 carbon atoms, a halogen-substituted alkylthio group, a cycloalkanothio group, a cycloalkanomethylthio group, a carboxyalkylthio group, an alkoxyalkylthio group or an alkyl-substituted aminoalkylthio group, and optionally substituted quinolium, isoquinolium, thiazolinium, N-alkylpyrrolidinium etc., or a heteroring attached via S, that is, a heterocyclic thio group, or a phenyl, a substituted phenyl group via S group.

The heteroring as herein used means a 5- or 6-membered ring containing 1-4 heteroatoms selected from O, S and N such as pyridyl, N-oxidopyridyl, pyrimidyl, pyridazinyl, N-oxidopyridazinyl, pyrazolyl, diazolyl, thiazolyl, thiadiazolyl, oxadiazolyl, triazolyl, tetrazolyl, triazinyl etc. or a bicyclic heteroring such as cycloalkenopyridyl, benzothiazolyl, benzimidazolyl, benzoxazolyl, triazaindolizinyl etc., and these heterorings may contain substituents, for example, a lower alkyl group of 1-3 carbon atoms, a halogen-substituted alkyl group, an alkoxy group, a halogen atom, a hydroxyl group, a mercapto group, an amino group, a carboxyl group, a carbamoyl group, a di-lower-alkylamino-lower-alkyl group of 1-3 carbon atoms, a carboxymethyl group, a hydroxyalkyl group, a sulfoalkyl group, a alkylmercapt group, a alkoxycarbonyl group, etc.

A represents a pyridiniumthio or substituted pyridiniumthio group of the formula:

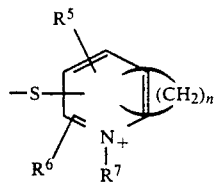

wherein n is 0 or an integer of 3-5, $R^5$ and $R^6$ may be the same or different and are a hydrogen atom, a halogen atom, or a lower alkyl group of 1-5 carbon atoms which may contain halogen atoms, and $R^7$ is a straight-chain or branched-chain alkyl group of 1-5 carbon atoms, a halogen- substituted alkyl group, a cyclopropyl group, a cyclopropylmethyl group, an alkenyl group, an oxygen atom or $-(CH_2)_mB$ wherein m is an integer of 0-3 and B is a hydroxyl group, an alkoxy group, an amino group, an alkyl-substituted amino group, a carboxyl group, a carbamoyl group, a sulfonic acid group, a sulfonamide group, a hydroxamic acid group, a cyano group, a thiol group, an alkylthio group, a methanesulfonylaminocarbonyl group or an acetamidosulfonyl group.

Specific examples of the substituent on the 3-position of the compounds of the formula (I) of this invention include the following, but it should be noted that they are not exhaustive examples.

Pyridiniummethyl, 4-methylpyridiniummethyl,
2,3-dimethylpyridiniummethyl,
2,3-cyclopentenopyridiniummethyl,
2,3-cyclohexenopyridiniummethyl,
4-carbamoylpyridiniummethyl,
3-carbamoylpyridiniummethyl,
4-methylthiopyridiniummethyl,
3-methylthiopyridiniummethyl,
2-methylthiopyridiniummethyl,
4-ethylthiopyridiniummethyl,
4-allylthiopyridiniummethy,2-allylthiopyridiniummethyl,
4-cyclopropylmethylthiopyridiniummethyl,
3-cyclopropylmethylthiopyridiniummethyl,
4-cyclopropylthiopyridiniummethyl,
4-cyclopentylthiopyridiniummethyl,
4-(2,2,2-trifluoroethyl)thiopyridiniummethyl,
4-(2-hydroxyethyl)thiopyridiniummethyl,
3-(2-hydroxyethyl)thiopyridiniummethyl,
2-(2-hydroxyethyl)thiopyridiniummethyl,
2-cyclopropylthiopyridiniummethyl,
4-trimethylsilylpyridiniummethyl,
3-trimethylsilylpyridiniummethyl,
4-trifluoromethylthiopyridiniummethyl,
4-(2-fluoroethyl)thiopyridiniummethyl,
4-carboxymethylthiopyridiniummethyl,
4-carbamoylmethylthiopyridiniummethyl,
4-(N,N-dimethylaminoethyl)thiopyridiniummethyl,
2,3-cyclopenteno-4-methylthiopyridiniummethyl,
2,3-cyclopenteno-4-ethylthiopyridiniummethyl,
2,3-cyclopenteno-4-allylthiopyridiniummethyl, 2,3-cyclopenteno 2-4-cyclopropyl-methylthiopyridiniummethyl,
2,3-cyclopenteno-4-cyclopropylthiopyridiniummethyl,
2,3 cyclopenteno-4-pentylthiopyridiniummethyl,
2,3-cyclopenteno-4-(2,2,2-trifluoroethyl) thiopyridiniummethyl,
2,3-cyclopenteno-4-(2-hydroxyethyl)thiopyridiniummethyl,
2,3-cyclopenteno-4-(2-fluoroethyl)thiopyridiniummethyl,
2,3-cyclopenteno-4-carboxymethylthiopyridiniummethyl,
2,3-cyclopenteno-4-carbamoylmethylthiopyridiniummethyl,
2,3-cyclopenteno-4-(N,N-dimethylaminoethyl) thiopyridiniummethyl,
2,3-cyclohexeno-4-methylthiopyridiniummethyl,
2,3-cyclohexeno-4-cyclopropylmethylthiopyridiniummethyl,
2,3-cyclohexeno-4-cyclopropylthiopyridiniummethyl,
2,3-cyclohexeno-4-(2-hydroxyethyl)thiopyridiniummethyl,
2,3-cyclohexeno-4-(2,2,2-trifluoroethyl) thiopyridiniummethyl,
2,3-cyclohexeno-4-carboxymethylthiopyridiniummethyl,
2,3-cyclohexeno-4-carbamoylmethylthiopyridiniummethyl,
5,6-cyclopenteno-2-methylthiopyridiniummethyl,
5,6-cyclopenteno-2-allylthiopyridiniummethyl,
5,6-cyclopenteno-2-cyclopropylthiopyridiniummethyl,
5,6-cyclopenteno-2-(2-hydroxyethyl)thiopyridiniummethyl, 5,6-cyclopenteno 2-(2-fluoroethyl)thiopyridinium-methyl,
5,6-cyclopenteno 2-carboxymethylthiopyridinium-methyl,
5,6-cyclopenteno-2-carbamoylmethylthiopyridinium-methyl, (quinolinium-1-yl)methyl,
(3-aminoquinolinium-1-yl)methyl,
(5-aminoquinolinium-1-yl)methyl,
(5-hydroxyquinolinium-1-yl)methyl,
(6-hydroxyquinolinium-1-yl)methyl,
(7-hydroxyquinolinium-1-yl)methyl,
(4-carbamoylquinolinium-1-yl)methyl,
( 5-trifluoromethylquinolinium-1-yl )methyl,
(isoquinolinium-2-yl)methyl,
(5-hydroxyisoquinolinium-2-yl)methyl,
(4-hydroxyisoquinolinium-2-yl)methyl,
(5-aminoisoquinolinium-2-yl)methyl,
(4-aminoisoquinolinium-2-yl)methyl,
(3-methylisoquinolinium-2-yl)methyl,
(5-hydroxyisoquinolinium-2-yl)methyl,
(8-hydroxyisoquinolinium-2-yl)methyl,
(4-carbamoylisoquinolinium-2-yl)methyl,
(5-trifluoromethylisoquinolinium-2-yl)methyl,
(thieno[3,2-c]pyridinium-5-yl)methyl,
(thieno[2,3-b]pyridinium-7-yl)methyl,
(thieno[3,2-b]pyridinium-4-yl)methyl,
(thieno[2,3-c]pyridinium-6-yl)methyl,
(thieno[3,4-b]pyridinium-4-yl)methyl,
(thieno[3,4-c]pyridinium-5-yl)methyl,
(4-methylthieno[2,3-b]pyridinium-7-yl)methyl,
(furo[2,3-c]pyridinium-6-yl)methyl,
(furo[3,2-c]pyridinium-5-yl)methyl,
(furo[2,3-b]pyridinium-7-yl)methyl,
(furo[3,2-b]pyridinium-4-yl)methyl,
(2-methylfuro[3,2-b]pyridinium-4-yl)methyl,
(2,4-dimethylfuro[2,3-b]pyridinium-4-yl)methyl,
(thiazolo[4,5-c]pyridinium-5-yl)methyl,
(2-aminothiazolo[4,5-c]pyridinium-5-yl)methyl,
(2-methylthiazolo[4,5-c]pyridinium-5-yl)methyl,
(1,3-dihydrofuro[3,4-b]pyridinium-4-yl)methyl,
(1,3-dihydropyrolo[3,4-b]pyridinium-4-yl)methyl,
(2-methyl-1,3-dihydropyrolo[3,4-b]pyridinium-4-yl)methyl, (2,2-dimethyl-1,3-dihydropyrolo[3,4-b]pyridinium-4yl)methyl,
(1,3-dihydrothieno[3,4-b]pyridinium-4-yl)methyl,
(2-oxo-1,3-dihydrothieno[3,4-b]pyridihium-4-yl)methyl,
(pyradinium-1-yl)methyl,
(3-methylpyradinium-1-yl)methyl,
(3,5-dimethylpyradinium-1-yl)methyl,
[3-(2-hydroxyethyl)aminopyradinium-1-yl]methyl,
(3-aminopyradinium-1-yl)methyl,
(3-dimethylaminopyradinium-1-yl)methyl,
(thiazolinium-3-yl)methyl,
(4-methylthiazolinium-3-yl)methyl,
(1-methylpyrolidinium-1-yl)methyl,
trimethylammoniummethyl,
N,N-dimethyl-N-(2-hydroxyethyl)ammoniummethyl,
N,N-dimethyl-N-allylammoniummethyl,
N,N-diethyl-N-methylammoniummethyl,
phenylthiomethyl, (4-hydroxyphenyl)thiomethyl,
(4-fluorophenyl)thiomethyl,
(1H-tetrazole-5-yl)thiomethyl,
(1-methyl-1H-tetrazole-5-yl)thiomethyl,
(1-amino-1H-tetrazole-5-yl)thiomethyl,
[1-(2-dimethylaminoethyl)-1H-tetrazole-5-yl]thiomethyl,
[1-(2-hydroxyethyl)-1H-tetrazole-5-yl]thiomethyl,
[1-(2-carboxyethyl)-1H-tetrazole-5-yl]thiomethyl,
(1-carboxymethyl-1H-tetrazole-5-yl)thiomethyl,
(1-carbamoylmethyl-1H-tetrazole-5-yl)thiomethyl,
(1-sulfomethyl-1H-tetrazole-5-yl)thiomethyl,
[1-(2-sulfoethyl)-1H-tetrazole-5-yl]thiomethyl,
(1-sulfamoylmethyl-1H-tetrazole-5- yl)thiomethyl,
(1,3,4-thiadiazole-5-yl)thiomethyl,
(2-methyl-1,3,4-thiadiazole-5-yl)thiomethyl,
(2-ethylthio-1,3,4-thiadiazole-5-yl)thiomethyl,
(2-carbamoyl-1,3,4-thiadiazole-5-yl)thiomethyl,
(2-ethoixycarbonyl-1,3,4-thiadiazole-5-yl)thiomethyl,
(2-ethoxy-1,3,4-thiadiazole-5-yl)thiomethyl,
(2-trifluoromethyl-1,3,4-thiadiazole-5-yl)thiomethyl,
(2-carboxy-1,3,4-thiadiazole-5-yl)thiomethyl,
(2-methylamino-1,3,4-thiadiazole-5-yl)thiomethyl,
(2-amino-1,3,4-thiadiazole-5-yl)thiomethyl,
(2-mercapto-1,3,4-thiadiazole-5-yl)thiomethyl,
(2-carbamoylmethyl-1,3,4-thiadiazole-5-yl)thiomethyl,
(1,2,3-thiadiazole-5-yl)thiomethyl,
(4-methyl-1,2,3-thiadiazole-5-yl)thiomethyl,
(4-carbamoyl-1,2,3-thiadiazole-5-yl)thiomethyl,
4-ethoxycarbonyl-1,2,3-thiadiazole-5-yl)thiomethyl,
(1,2,4-thiadiazole-5-yl)thiomethyl,
(3-methyl-1,2,4-thiadiazole-5-yl)thiomethyl,
(3-phenyl-1,2,4-thiadiazole-5-yl)thiomethyl,
(thiazole-2-yl)thiomethyl,
(4-methylthiazole-2-yl)thiomethyl,
(4-phenylthiazole-2-yl)thiomethyl,
(4-trifluoromethylthiazole-2-yl)thiomethyl,
(4-carboxymethylthiazole-2-yl)thiomethyl,
(5-methylthiazole-2-yl)thiomethyl,
(5-phenylthiazole-2-yl)thiomethyl,
(thiazole-5-yl)thiomethyl,
(4-carbamoylthiazole-5-yl)thiomethyl,
(4-ethoxycarbonyl-5-yl)thiomethyl,
(4-carboxy-3-hydroxyisothiazole-5-yl)thiomethyl,
(4-cyano-3-hydroxyisothiazole-5-yl)thiomethyl,
(1,3,4-oxadiazole-5-yl)thiomethyl,
(2-methyl-1,3,4-oxadiazole-5-yl)thiomethyl,
(2-phenyl-1,3,4-oxadiazole-5-yl)thiomethyl,
(2-carboxymethyl-1,3,4-oxadiazole-5-yl)thiomethyl,
(1,2,4-oxadiazole-5-yl)thiomethyl,
(3-methyl-1,2,4-oxadiazole-5-yl)thiomethyl,
(3-phenyl-1,3,4-oxadiazole-5-yl)thiomethyl,
(oxazole-2-yl)thiomethyl,
(4-methyloxazole 2-yl)thiomethyl,
(pyrazole-5-yl)thiomethyl,
(1-methylimidazole-2-yl)thiomethyl,
(1H-1,2,3-triazole-5-yl)thiomethyl,
(1-methyl-1H-1,2,3-triazole-5-yl)thiomethyl,
(1H-1,2,4-triazole-5-yl)thiomethyl,
(1-methyl-1H-1,2,4-triazole-5-yl)thiomethyl,
(4-methyl-3-trifluoromethyl-4H-1,2,4-triazole-5-yl)thiomethyl, (1H-1,3,4-triazole-5-yl)thiomethyl
(1-methyl-1H-1,3,4-triazole-5-yl)thiomethyl,
(1-carboxymethyl-1H-1,3,4-triazole-5-yl)thiomethyl,
(1-carbamoylmethyl-1H-1,3,4-triazole-5-yl)thiomethyl,
(2-methyl-1H-1,3,4-triazole-5-yl)thiomethyl,
(2-carboxymethyl-1H-1,3,4-triazole-5-yl)thiomethyl,
(2-phenyl-1H-1,3,4-triazole-5-yl)thiomethyl,
(2,5-dihydro-2-methyl-5-oxo-6-hydroxy-1,2,4-triazin-3yl)thiomethyl, (4,5-dihydro-4-methyl-5-oxo-6-hydroxy1,2,4-triazine-3-yl) thiomethyl,
(2,3-dihydro-3-methyl-2-oxo-6-hydroxy-1,3,5-triazine-4-yl)thiomethyl, (3,4-dihydro-4-methyl-1,1,3-trioxo-2H-1,2,4,6-thiatriazine-5-yl)-thiomethyl,
(5-methyl-s-triazolo[1,5-a]pyrimidine-7-yl)thiomethyl,
(2-carboxy-5-methyl-s-triazolo[1,5-a]pyrimidin-7-yl)thiomethyl, (pyridazine-3-yl)thiomethyl, (2-oxypyridazine-3-yl)thiomethyl,
(pyrimidine-2-yl)thiomethyl,
(benzothiazole-2-yl)thiomethyl,
(benzimidazole-2-yl)thiomethyl,
(benzoxazole-2-yl)thiomethyl,
(3H-4-quinazoline-2-yl)thiomethyl,
(pyridine-4-yl)thiomethyl, (pyridine-3-yl)thiomethyl,
(pyridine-2-yl)thiomethyl,
(3- methylpyridine-4-yl)thiomethyl,
(2,3-dimethylpyridine-4-yl)thiomethyl,
(2-carboxypyridine-4-yl)thiomethyl,
(2-carbamoylpyridine-4-yl)thiomethyl,
(2,3-cyclopentenopyridine-4-yl)thiomethyl,
(pyridin-N-oxid-4-yl)thiomethyl,
(5,6-cyclopentenopyridine-2-yl)thiomethyl,
(2,3-cyclohexenopyridine-4-yl)thiomethyl,
(5,6-cyclohexenopyridine-2-yl)thiomethyl,
(1-methylpyridinium-4-yl)thiomethyl,
(1-methylpyridinium-2-yl)thiomethyl,
(1-methylpyridinium-3-yl)thiomethyl,
(1-ethylpyridinium-4-yl)thiomethyl,
(1-allylpyridinium-4-yl)thiomethyl,
[1-(2,2,2-trifluoroethyl)pyridinium-4-yl]thiemethyl,
(1-carboxymethylpyridinium-4-yl)thiomethyl,
(1-carbamoylmethylpyridinium-4-yl)thiomethyl,
[1-(1-carboxyethyl)pyridinium-4-yl]thiomethyl,
[1-(2-hydroxyethyl)pyridinium-4-yl]thiomethyl,
(1-dimethylaminoethylpyridinium-4-yl)thiomethyl,
(1-cyclopropylpyridinium-4-yl)thiomethyl,
(1-cyclopropylmethylpyridinium-4-yl)thiomethyl,
(1-methylthiomethylpyridinium-4-yl)thiomethyl,
(1-cyanomethylpyridinium-4-yl)thiomethyl,
[1-(2-fluoroethyl)pyridinium-4-yl]thiomethyl,
(1-hydroxyaminocarbonylmethylpyridinium-4-yl)thiomethyl,
[1-(2-sulfoethyl)pyridinium-4-yl]thiomethyl,
(1-sulfomethylpyridinium-4-yl)thiomethyl,
(1-sulfamoylmethylpyridinium-4-yl)thiomethyl,
(1-N,N-dimethylsulfamoylmethylpyridinium-4-yl)thiomethyl,
(2,6-dimethyl-1-carboxymethylpyridinium-4-yl)thiomethyl
(3,5-dimethyl-1-carboxymethylpyridinium-4-yl)thiomethyl,
(2-carboxy-1-methylpyridinium-4-yl)thiomethyl,
(1-ethylpyridinium-3-yl)thiomethyl,
(1-allylpyridinium-3-yl)thiomethyl,
(1-cyclopropylpyridinium-3-yl)thiomethyl,
[1-(2-hydroxyethyl)pyridinium-3-yl]thiomethyl,
(1-carboxymethylpyridinium-3-yl)thiomethyl,
(1-carbamoylmethylpyridinium-3-yl)thiomethyl,
[1-(2-fluoroethyl)pyridinium-3-yl]thiomethyl,
[1-(2,2,2-trifluoroethyl)pyridinium-3-yl]thiomethyl,
(1-sulfomethylpyridinium-3-yl)thiomethyl,
(1-sulfamoylmethylpyridinium-3-yl)thiomethyl,
[1-(2-sulfoethyl)pyridinium-3-yl]thiomethyl,
(1-ethylpyridinium-2-yl)thiomethyl,
(1-allylpyridinium-2-yl)thiomethyl,
(1-cyclopropylpyridinium-2-yl)thiomethyl,
[1-(2-hydroxyethyl)pyridinium-2-yl]thiomethyl,
(1-carboxymethylpyridinium-2-yl)thiomethyl,
(1 carbamoylmethylpyridinium-2-yl)thiomethyl,
[1-(1-carboxyethyl)pyridinium-2-yl]thiomethyl,
[1-(2-fluoroethyl)pyridinium-2-yl]thiomethyl,
[1-(2,2,2-trifluoroethyl)pyridinium-2-yl]thiomethyl,
(1-sulfomethylpyridinium-2-yl)thiomethyl,
(1-sulfamoylmethylpyridinium-2-yl)thiomethyl,
[1-(2-sulfoethyl)pyridinium-2-yl]thiomethyl,
(2,3-cyclopeteno-1-methylpyridinium-4-yl)thiomethyl,
(2,3-cyclopeteno-1-ethylpyridinium-4-yl)thiomethyl,
(2,3-cyclopeteno-1-allylpyridinium-4-yl)thiomethyl,
[2,3-cyclopeteno-1-(2,2,2-trifluoroethyl)pyridinium-4-yl]thiomethyl,
(2,3-cyclopeteno-1-carboxymethylpyridinium-4-yl)thiomethyl,
(2,3-cyclopeteno-1-carbamoylmethylpyridinium-4-yl)thiomethyl, [2,3-cyclopeteno-1-(2-hydroxyethyl)-pyridinium-4-yl]thiomethyl,
(2,3-cyclopeteno-1-dimethylaminoethylpyridinium-4-yl)thiomethyl, (2,3-cyclopeteno-1-cyclopropyl-pyridinium-4-yl)thiomethyl, (2,3-cyclopeteno-1-cycloproipylmethylpyridinium-4-yl)thiomethyl, (2,3-cyclopeteno-1-cyanomethylpyridinium-4-yl)thiomethyl,
(2,3-cyclopeteno-1-sulfomethylpyridinium-4-yl)thiomethyl, [2,3-cyclopeteno-1-(2-fluoroethyl) pyridinium-4-yl]thiomethyl, [2,3-cyclopeteno-1-(2-sulfoethyl)pyridinium-4-yl]thiomethyl,
[2,3 cyclopeteno-(2-sulphamoylethyl)pyridinium-4-yl]thiomethyl,
(5,6-cyclopeteno-1-methylpyridinium-2-yl)thiomethyl,
(5,6-cyclopeteno-1-ethylpyridinium-2-yl)thiomethyl,
(5,6-cyclopeteno-1-allylpyridinium-2-yl)thiomethyl,
[5,6-cyclopeteno-1-(2-fluoroethyl)pyridinium-2-yl]thiomethyl, [5,6-cyclopeteno-(2-hydroxyethyl)pyridinium-2-yl]thiomethyl, (5,6-cyclopeteno-1-carboxymethylpyridinium-2-yl)thiomethyl, (2,3-cyclohexeno-1-methylpyridinium-4-yl)thiomethyl, (2,3-cyclohexeno-1-carboxymethylpyridinium-4-yl) thiomethyl, (2,3-cyclohexeno-1-carbamoylmethylpyridinium -4-yl)thiomethyl,
[2,3-cyclohexeno-1-(2-hydroxyethyl)pyridinium-4-yl]thiomethyl, [2,3-cyclohexeno-1-(dimethylaminoethyl) pyridinium-4-yl]thiomethyl,
(2,3-dihydro-1H-indolidinium-5-yl)thiomethyl.

Synthesis of a protected form of 2-hydroxymethyl-1,5-dihydroxy-4-pyridone which is one of the constituting components for the substituent on the 7-position was conducted according to the process disclosed in Japanese Patent Application No. 60-140989 by the present inventors.

That is, it may be obtained by reacting a protected form of kojic acid (II) with hydroxylamine hydrochloride or $R^9ONH_2$ or a salt thereof in the presence of pyridine etc.

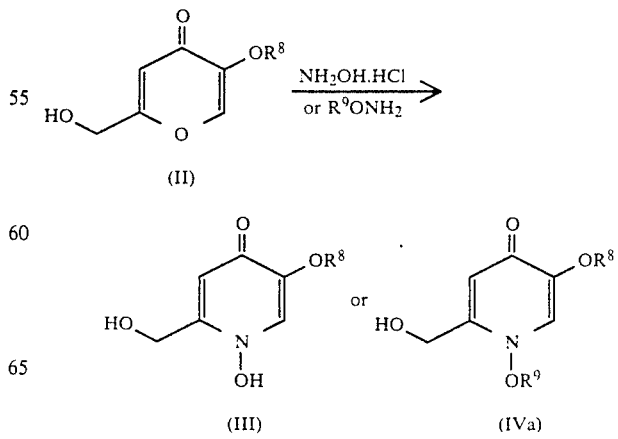

wherein $R^8$ and $R^9$ are a removable protecting group such as benzyl, p-nitrobenzyl, o-nitrobenzyl, p-methoxybenzyl, benzhydryl, etc.

Further, in the reaction of the compound of the formula (III) and $R^9X$ (wherein X is a halogen atom or a diazo group), the product may be obtained as (IVa) or (IVb) or a mixture thereof depending on the kind of $R^9X$, the reaction solvent and the reaction conditions such as the temperature.

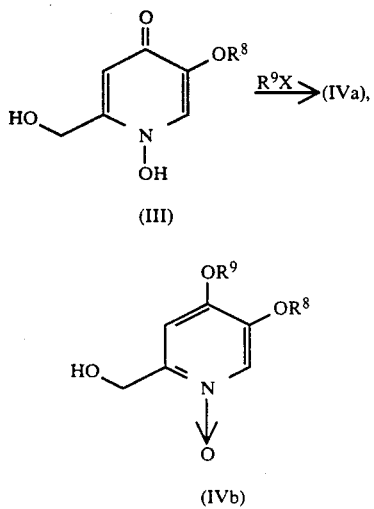

The cephalosporin compounds of the general formula (I) of this invention may be produced by the following process A) or B).

A) A compound of the general formula (Va) or (Vb):

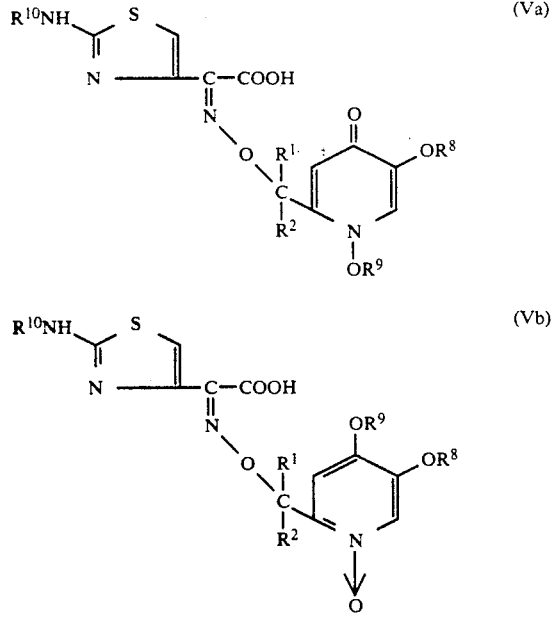

wherein $R^{10}$ is a hydrogen atom or a protecting group for the amino group and $R^1$, $R^2$, $R^8$ and $R^9$ are as defined above, or a reactive derivative of the carboxylic acid is reacted with a compound of the general formula (VI):

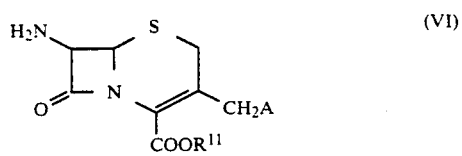

wherein $R^{11}$ is a hydrogen atom or a protecting group for the carboxyl group and A is as defined above, or a salt or silylated product thereof, and thereafter, the protecting group is removed.

B) A compound of the general formula (VIIa) or (VIIb):

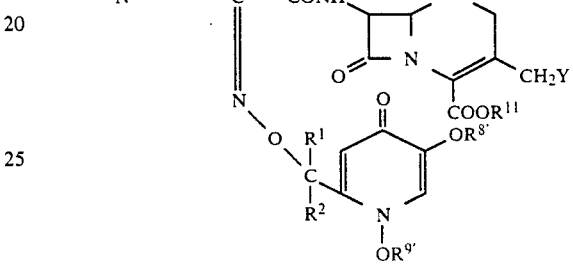

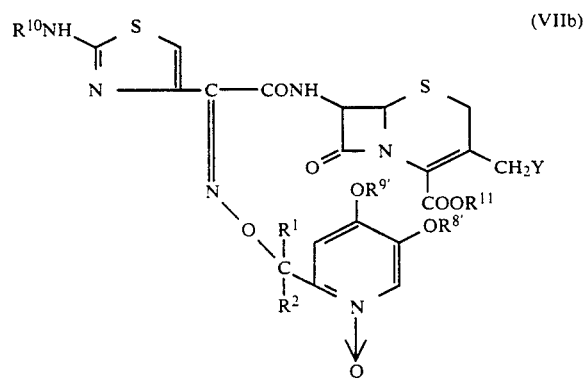

wherein Y is an acetoxy group or a halogen atom, $R^{8'}$ is a hydrogen atom or $R^8$, $R^{9'}$ is a hydrogen atom or $R^9$ and $R^1$, $R^2$, $R^8$, $R^9$, $R^{10}$ and $R^{11}$ are as defined above is reacted with a nucleophilic compound, and thereafter, if needed, the protecting group is removed, whereby the compound of the general formula (I) is produced. The nucleophilic compound as herein used is a compound corresponding to A in the general formula (I).

As the protecting groups for the amino group and the carboxyl group in the above-described general formula, those employed for this purpose in the field of β-lactam and peptide synthesis are appropriately employed.

Examples of the protecting group for the amino group include phthaloyl, formyl, monochloroacetyl, dichloroacetyl, trichloroacetyl, methoxycarbonyl, ethoxycarbonyl, t-butoxycarbonyl, trichloroethoxycarbonyl, benzyloxycarbonyl, p-nitrobenzyloxycarbonyl, diphenylmethyloxycarbonyl, methoxymethyloxycarbonyl, trityl, trimethylsilyl etc., and examples of the protecting group for the carboxyl group include t-butyl, t-amyl, allyl, benzyl, p-nitrobenzyl, p-methoxybenzyl, benzhydryl, phenyl, p-nitrophenyl, methoxymethyl, ethoxymethyl, benzyloxymethyl, acetoxymethyl, methylthiomethyl, trityl, trichloroethyl, trimethylsilyl, dimethylsilyl etc.

The condensation reaction of the general formulae (Va) or (Vb) and (VI) in Process A may be conducted by using a usual method for acylation used for penicillins and cephalosporins.

Examples of the reactive derivative include acid halides, acid anhydrides, active amides, active esters etc. Preferred examples thereof include acid chlorides, acid bromides, mixed acid anhydrides of e.g. acetic acid, pivalic acid, isovaleric acid, trichloroacetic acid etc., active amides with pyrazole, imidazole, dimethylpyrazole, benzotriazole etc., and active esters with p-nitrophenyl ester, 2,4-dinitrophenyl ester, trichlorophenyl ester, 1-hydroxy-1H-pyridone, N-hydroxysuccinimide, N-hydroxybenzotriazole, N-hydroxyphthalimide etc.

Further, in this reaction, where the compound of the general formula (Va) or (Vb) is used in the form of a free acid, it is preferred to carry out the reaction in the presence of a condensing agent; that is, the reaction may be carried out in the presence of a condensing agent such as reagents produced by the reaction of a carbodiimide compound, e.g., N,N-dicyclohexylcarbo-diimide, N-cyclohexyl-N'-morpholinoethylcarbodiimide, N-cyclohexyl-N'-(4-diethylaminocyclohexyl)carbodiimide etc. or an amide compound, e.g., N-methylformamide, N,N-dimethylforamide etc. with a halide such as thionyl chloride, phosphorus oxychloride, phosgene etc. (the so-called Vilsmeier reagents).

Of the reactive derivatives in this reaction, the reaction involving the acid halide or the acid anhydride requires the presence of an acid binder, and examples of the acid binder include organic bases such as triethylamine, trimethylamine, ethylisopropylamine, N,N-dimethylamine, N-methylmorpholine, pyridine etc., hydroxides of e.g. sodium, potassium, calcium etc., alkali metal salts such as alkali metal carbonates, bicarbonates etc. and oxiranes such as ethylene oxide, propylene oxide etc.

This reaction is generally carried out in a solvent which does not exert any adverse influences on the reaction, and examples of the solvent which may be used include water, acetone, acetonitrile, dioxane, tetrahydrofuran, ethyl acetate, methylene chloride, chloroform, dichloroethane, N,N-dimethylformamide, N,N-dimethylacetamide, dimethylsulfoxide or mixed solvents thereof.

Although the reaction temperature is not particularly restricted, the reaction is generally conducted at $-30°$ C. to 40° C., and for the reacting time, the reaction reaches completion in 30 minutes to 10 hours.

The method for removing the protecting group of the thus obtained acylated product may be chosen among a method using an acid, a method using a base, a method using hydrazine etc. depending on the kind of protecting group, and these methods may be conducted by appropriately selecting the conventional methods used in the field of $\beta$-lactam and peptide synthesis.

The compound of the general formula (Va) or (Vb) may be obtained by reacting a compound of the general formula (VIII):

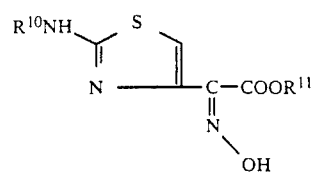

wherein $R^{10}$ and $R^{11}$ are as defined above or a salt thereof with a compound of the general formula (IXa) or (IXb):

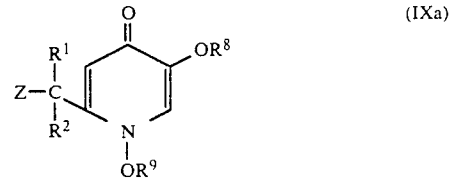

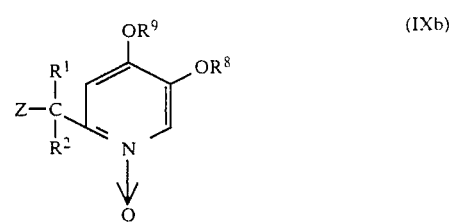

wherein Z is a halogen atom or a sulfonate group such as mesyloxy, tosyloxy, trifluoromesyloxy etc. and thereafter, if necessary, removing the protecting group for the carboxylic acid.

This condensation reaction may be conducted at a temperature in the range of $-50°$ C. to 70° C. in a solvent and, if necessary, in the presence of a base. The base and the solvent used in this reaction may be chosen among bases and solvents used for the acylation reaction in Process A. The reaction of the general formula (VIIa) or (VIIb) and the nucleophilic compound in Process B may be chosen from methods conventionally employed in the cephalosporin chemistry. That is, the reaction where Y is an acetoxy group in the general formula (VIIa) or (VIIb) is generally preferably conducted in a polar solvent such as water, phosphate buffers, acetone, acetonitrile, N,N-dimethylformamide, N,N-dimethylacetamide, tetrahydrofuran, dimethylsulfoxide, dioxane, methanol, ethanol etc. or mixed solvents thereof with water.

It is preferred to carry out the reaction in the vicinity of neutrality, and while the reaction temperature is not particularly restricted, it is suitable to conduct at room temperature to about 80° C.

The time required for this reaction depends on the reaction conditions, but in general, it is 1–10 hours.

Further, this reaction may be promoted by conducting it in the presence of an alkali metal halide such as sodium iodide, potassium iodide etc.

Further, where the intended product is to be produced from the compound of the general formula (VIIa) or (VIIb) wherein Y is a halogen atom, it is preferred to conduct the reaction in a solvent such as acetone, dioxane, tetrahydrofuran, ethyl acetate, acetonitrile, N,N-dimethylformamide, N,N-dimethylacetamide, dimethylsulfoxide etc. under anhydrous conditions. The reaction is generally preferably conducted at 0°–50° C. and it reaches completion in 1–5 hours.

The compound of the general formula (I) obtained as above may be separated from the reaction mixture in a conventional manner.

For example, it is effected by appropriately combining such methods as purification using an absorbing resin, e.g., Amberlite XAD-2 (produced by Rohm & Haas), Diaion HP-20 (produced by Mitsubishi Chemical Industries) etc., precipitation, crystallization and the like.

Antibacterial agents containing the compounds of the general formula (I) or salts thereof as the main ingredient may be mainly used in various pharmaceutical forms, for example, injections such as intravenous, intramuscular injections etc., oral forms such as capsules, tablets, powders etc., as well as intrarectal dosage forms, oily suppositories, water-soluble suppositories etc. These various forms may be prepared in a conventional manner by using conventional excipients, fillers, binders, wetting agents, disintegrants, surfactants, lubricants, dispersants, buffers, preservatives, solubilizing aids, antiseptics, flavoring agents, analgesics etc. Specific embodiments for the production process will be described in more detail in the examples described below.

The dosage is appropriately and individually determined in consideration of the severeness of the disease, the age, the sex etc., but for example, the daily dose for an adult is usually 250–3000 mg, and it is administered in portions 1–4 times a day.

EXAMPLES

This invention is described in more detail by the following examples, but it should be noted that these examples are mere examples and various changes and modifications may be made without departing from the scope of the invention.

In the examples, the NMR data are obtained by using 400 MHz NMR and indicated as the $\delta$ values against the peak value for water taken as 4.82 in the case of deuterium oxide or as the $\delta$ values against the TMS standard in the case of other deuterated solvents.

REFERENCE EXAMPLE 1

5-p-Methoxybenzyloxy-1-hydroxy-2-hydroxymethyl-4-pyridone (a) 42.6 9 of kojic acid is dissolved in 350 ml of N-dimethylformamide, then 82.8 g of anhydrous potassium carbonate and 55 g of p-methoxybenzyl chloride are added thereto, and reacted at 70°–75° C. for 1.5 hours. After the reaction, the reaction mixture is concentrated to about half the volume, and added dropwise to 700 ml of water with ice cooling. The formed precipitates are filtered off, washed with water and ethyl acetate and dried to obtain 59.9 g of 5-p-methoxybenzyloxy-2-hydroxymethyl-4-pyrone.

NMR(CDCl$_3$)$\delta$; 3,80(3H,s), 4.43(2H,s), 4.96(2H,s), 6.50(1H,s), 6.88(2H,d), 7.30(2H,d), 7.51(1H,s)

(b) 39.3 g of 5-p-methoxybenzyloxy-2-hydroxymethyl-4-pyrone is dissolved in 600 ml of pyridine, then 52.2 g of hydroxylamine hydrochloride is added thereto, and reacted at 70°–75° C. for 2.5 hours. After the reaction, the reaction mixture is concentrated to about 100 ml and, after adding 100 ml of water thereto, added to a mixed solution of 75 ml of hydrochloric acid and 225 ml of water with ice cooling. The pH is adjusted to 2–2.5, and stirring is conducted at the same temperature for 30 minutes. The formed crystals are filtered off, washed with water and then dried to obtain 16.6 f of the title compound.

NMR(DMSO-d$_6$)$\delta$; 3.76(3H,s), 4.46(2H,s), 5.03(2H,s), 6.86(1H,s), 6.93(2H,d), 7.37(2H,d), 7.97(1H,s).

REFERENCE EXAMPLE 2

4-Diphenylmethyloxy-5-p-methoxybenzyloxy-2-hydroxymethyl pyridine-N-oxide 44.3 g of 5-p methoxybenzyloxy-1-hydroxy-2-hydroxymethyl-4-pyridone is suspended in 320 ml of methyl cellosolve (2-methoxyethanol) and 33.4 ml of triethylamine is added thereto to dissolve. Then, 150 ml of a methyl cellosolve solution containing 46.6 g of diphenyldiazomethane is added thereto and reacted at 60° C. for 5 hours.

After the reaction, the reaction mixture is concentrated to about 100 ml, and 200 ml of a mixed solution of ethyl acetate and isopropyl ether (1:1) is added thereto. The formed crude crystals are filtered off, then washed with a mixed solution of ethyl acetate and isopropyl ether (1:1) and isopropyl ether, and dried. This is suspended in 500 ml of dichloromethane, and the insolubles are removed by filtration. The dichloromethane solution is concentrated to a small volume, then ethyl acetate is added thereto, and the formed crystals are filtered off and dried to obtain 42 g of the intended title compound.

NMR(CDCl$_3$)$\delta$; 3.82(3H,s), 4.57(2H,s), 5.06(2H,s), 6.28(1H,s), 6.69(1H,s), 6.89(2H,d), 7.2-7.5(12H,m), 7.91(1H,s).

REFERENCE EXAMPLE 3

1,5-Di-p-methoxybenzyloxy-2-hydroxymethyl-4-pyridone 27.7 g of 5-p-methoxybenzyloxy-1-hydroxy-2-hydroxymethyl-4-pyridone is suspended in 300 ml of N,N-dimethylformamide, then 27.7 g of anhydrous potassium carbonate and 17.3 g of p-methoxybenzyl chloride are added, and reacted at room temperature for 4 hours. The reaction mixture is concentrated to a small volume, then, after adding 600 ml of chloroform, washed with water and then dried on anhydrous magnesium sulfate and further concentrated to about 200 ml. 200 ml of isopropyl ether is added thereto, and the formed crystals are filtered off and dried to obtain 38.9 g of the intended title compound.

NMR(CDCl$_3$)$\delta$; 3.75(3H,2), 3.80(3H,s), 4.49(2H,s), 4.90(2H,s), 5.01(2H,s), 6.47(1H,s), 6.82(2H,d), 6.87(2H,d), 6.98(1H,s), 7.20(2H,d), 7.23(2H,d),

REFERENCE EXAMPLE 4

1- Diphenylmethyloxy-5 p-methoxybenzyloxy-2-hydroxymethyl-4-pyridone 5.54 g of 5-p-methoxybenzyloxy-1-hydroxy-2-hydroxymethyl-4-pyridone is suspended in 40 ml of N,N-dimethylformamide, and then 2.24 g of potassium t-butoxide is added with ice cooling to dissolve. 4.94 g of benzhydryl bromide is added thereto and reacted at room temperature for 2.5 hours.

After the reaction, the reaction mixture is concentrated to about 20 ml, which is then added dropwise to a mixed solution of ethyl acetate (200 ml) and water (100 ml). The formed precipitates are filtered off, washed with water and ethyl acetate, and then dried to obtain 7.29 g of the intended title compound.

NMR(CDCl₃)δ; 3.78(3H,s), 4.51(2H,s), 4.59(2H,s), 6.18(1H,s), 6.58(1H,s), 6.63(1H,s), 6.82(2H,d), 7.16(2H,d), 7.3–7.5(10H,m).

EXAMPLE 1

(6R,7R)-7-[(Z)-2-(2-Aminothiazole-4-yl)-2-(1,5-dihydroxy-4-pyridone-2-yl) methoxyiminoacetamido]-3-(1-methylpyridinium-4-yl)thiomethyl-ceph-3em-4-carboxylate (a) 2.2 g of 4-diphenylmethyloxy-5-p-methoxybenzyloxy-2-hydroxymethylpyridine-N-oxide is suspended in 50 ml of dichloromethane, 1 ml of thionyl chloride and one drop of N,N-dimethylformamide are added thereto with ice cooling, and reacted at the same temperature for 3 hours. 40 ml of a saturated sodium bicarbonate aqueous solution and 50 ml of dichloromethane are added thereto. The dichloromethane layer is washed with water, then dried on anhydrous magnesium sulfate, and concentrated to dryness under reduced pressure. The residue is dissolved in 40 ml of N,N-dimethylformamide, then 2.1 g of allyl(Z)-2-(2-tritylaminothiazole-4-yl)2-hydroxyiminoacetate and 1.24 g of potassium carbonate anhydride are added thereto, and reacted overnight at room temperature. 200 ml of chloroform is added to the reaction mixture. It is washed with water, dilute hydrochloric acid and water successively, dried anhydrous on magnesium sulfate, and then concentrated to dryness under reduced pressure.

The residue is purified by silica gel column chromatography to obtain 2.18 g of allyl(Z)-2-(2-tritylaminothiazole-4-yl)-2-(4-diphenylmethyloxy -5-p-methoxybenzyloxypyridine-N-oxid-2-yl)methoxyiminoacetate.

NMR(CDCl₃)δ; 3.83(3H,s), 4.89(2H,d), 5.04(2H,s), 5.37(2H,dd), 5.38(2H,s), 6.0(1H,m), 6.40(1H,s), 6.57(1H,s), 6.90(2H,d), 6.93(1H,s), 6.96(1H,s), 7.1–7.5(27H,m), 7.87(1H,s).

(b) 1.74 g of the allyl ester compound obtained in (a) is dissolved in 15 ml of dichloromethane and 15 ml of ethyl acetate, 450 mg of potassium 2-ethylhexanoate and 60 mg of palladium tetrakistriphenylphosphine are added thereto, and reacted at room temperature for an hour. 150 ml of chloroform is added to the reaction mixture. 50 ml of water is added, and 6N hydrochloric acid is added so that the pH of the aqueous layer becomes 2 followed by washing. After washing with water, it is dried on anhydrous magnesium sulfate, and then concentrated to a small volume. Ether is added thereto, the formed crystals are filtered off, washed with a mixed solution of ether ー dichloromethane (4:1) and then dried to obtain 1.36 g of (Z)-2-(2-tritylaminothiazole-4-yl)-2-(4-diphenylmethyloxy-5-p methoxybenzyloxypyridine-N-oxid-2-yl)methoxyiminoacetic acid.

NMR(DMSO-d₆)δ; 3.76(3H,s), 5.01(2H,s), 5.16(2H,s), 6.80(1H,s), 6.96(2H,d), 7.1–7.5(29H,m), 8.06(1H,s)

(c) 1.15 g of the above product is dissolved in 30 ml of dichloromethane, then 730 mg of a p-toluenesulfonate salt of p-methoxybenzyl(6R,7R)-7-amino-3-chloromethyl-ceph-3-em-4-carboxylate and 0.54 ml of pyridine are added thereto at −5° C., and stirred for 10 minutes. Thereafter, at −10° to −15° C., 0.14 ml of phosphorus oxychloride is added, and reacted for an hour. After the reaction, 100 ml of ethyl acetate is added followed by washing twice with 50 ml portions of 15% aqueous NaCl. It is dried on anhydrous magnesium sulfate, and then concentrated to dryness to obtain 1.6 g of p-methoxybenzyl(6R,7R)-7-[(Z)-2-(2-tritylamino-thiazole-4-yl) -2-(4-diphenylmethyloxy-5-p-methoxybenzyloxypyridine-N-oxide-2-yl) methoxyiminoacetamido]-3-chloromethyl-ceph-2-em-4-carboxylate.

NMR(CDCl₃)δ; 3.36(2H,ABq), 3.80(3H,s), 3.83(3H,s), 4.45(2H,ABq), 4.97(1H,d), 5.02(2H,ABq), 5.21(2H, ABq), 5.82(1H,dd), 6.90(4H,m), 7.1–7.5(31H,m), 7.87(1H,s).

(d) 265 mg of the 3-chloromethyl compound obtained in (c) is dissolved in 0.55 ml of dimethylsulfoxide, 30 mg of 1-methyl-4-thiopyridone is added thereto, and reacted at room temperature for 1.5 hours. 30 ml of dichloromethane is added to the reaction mixture, which is then washed twice with 10 ml portions of 15% saline. It is dried on anhydrous magnesium sulfate, concentrated to about 3 ml, and added dropwise to 8 ml of ethyl acetate. The formed precipitates are filtered off, and dried to obtain 190 mg of p-methoxybenzyl(6R,7R)-7-[(Z)- 2-(2-tritylaminothiazole-4-yl) -2-(4-diphenylmethyloxy-5-p-methoxybenzyloxypyridine-N-oxid-2-yl) methoxyiminoacetamido]-3-(1-methylpyridinium-4-yl) thiomethyl-ceph-3-em-4 carboxylate. It is suspended in 14 ml of anisole, 0.43 ml of trifluoroacetic acid is added, and reacted at room temperature for 30 minutes. The reaction mixture is added dropwise to 6 ml of isopropyl ether, the formed precipitates are filtered off, washed with isopropyl ether, and dried. 135 mg of the obtained precipitates are dissolved in 3 ml of water, and after adding 1 ml of a saturated sodium bicarbonate aqueous solution with ice cooling, stirred for 10 minutes. It is purified by HP-20 column chromatography (eluted with 5% aqueous acetone) to obtain 35 mg of the intended title compound as a sodium salt.

NMR(DMSO-d₆)δ; 3.44(2H,ABq), 4.20(3H,s), 4.29(2H,ABq), 5.11(1H,d), 5.29(2H,ABq), 5.75(1H,d), 6.72(1H,s), 7.04(1H,s), 7.62(1H,s), 7.82(2H,d), 8.39(2H,d),

Compounds of the following Examples 2–13 are obtained treating in a manner similar to that in Example 1 except that the 1-methyl-4-thiopyridone in (d) of Example 1 is replaced by reagents [A] respectively.

EXAMPLE 2

(6R,7R)-7-[(Z)-2-(2-Aminothiazole-4-yl)-2-(1,5-dihydroxy-4-pyridone-2-yl) methoxyiminoacetamido]-3-(1-ethylpyridinium-4-yl)thiomethyl-ceph-3-em-4-carboxylate

[A] 1-Ethyl-4-thiopyridone
NMR(D₂O)δ; 1.57(3H,t), 3.44(2H,ABq), 4.29(2H,ABq), 4.45(2H,q), 5.11(1H,d), 5.28(2H,ABq), 5.74(1H,d), 6.71(1H,s), 7.01(1H,s), 7.61(1H,s), 7.82(2H,d), 8.45(2H,d),

EXAMPLE 3

(6R,7R)-7-[(Z)-2-(2 Aminothiazole-4-yl)-2-(1,5-dihydroxy-4-pyridone-2-yl) methoxyiminoacetamido]-3-[1-(2-hydroxyethyl) pyridinium-4-yl]thiomethyl-ceph-3-em-4-carboxylate A] 1-(2-Hydroxyethyl)-4-thiopyridone
NMR(D₂O)δ; 3.44(2H,ABq), 4.01(2H,m), 4.30(2H,ABq), 4.52(2H,m), 5.11(1H,d), 5.27(2H,ABq), 5.74(1H,d), 6.70(1H,s), 7.02(1H,s), 7.59(1H,s), 7.85(2H,d), 8.43(2H,d).

EXAMPLE 4

(6R,7R)-7-[(Z)-2-(2-Aminothiazole-4-yl)-2-(1,5-dihydroxy-4-pyridone-2-yl)methoxyiminoacetamido]-3-([(2,3-cyclopenteno-1-methylpyridinium-4-yl)thiomethylceph-3-em-4-carboxylate

[A] 1-methyl-cyclopentano[b]4-thopyridone
NMR($D_2O$)δ; 2.21(2H,m), 2.97(2H,m), 3.16(2H,m), 3.54(2H,ABq), 4.03(3H,s), 4.31(2H,s), 5.17(1H,d), 5.28(2H,bs), 5.71(1H,d), 6.70(1H,s), 6.92(1H,s), 7.59(X1H,s), 7.75(1H,d), 8.16(1H,d).

EXAMPLE 5

(6R,7R)-7-[(Z)-2-(2-Aminothiazole-4-yl)-2-(1,5-dihydroxy-4-pyridone-2-yl)methoxyiminoacetamido]-3-(1-methyl-1H-tetrazole-5-yl)thiomethyl-ceph-3-em-4-carboxylic acid

[A] 5-Mercapto-1-methyl 1H-terazole
NMR($D_2O$)δ: 3.43(2H,ABq), 4.05(3H,s), 4.29(2H,ABq), 5.13(1H,d), 5.30(2H,ABq), 5.74(1H,d), 6.70(1H,s), 7.02(1H,s), 7.61(1H,s).

EXAMPLE 6

(6R,7R]-7-[(Z)-2-(2-Aminothiazole-4-yl)2-(1,5dihydroxy-4-pyridone-2-yl)methoxyiminoacetamido]-3-(1,2,3-thiadiazole-5-yl)thiomethyl-ceph-3-em-4-carboxylic acid

[A] 5 Mercapto-1,2,3-thiadiazole
NMR($D_2O$)δ; 3.47(2H,ABq), 4.16(2H,ABq), 5.13(1H,d), 5.32(2H, ABq), 5.76(1H,d), 6.81(1H,s), 7.09(2H,s), 7.68(1H,s), 8.74(1H,s).

EXAMPLE 7

(6R,7R)-7-[(Z)-2-(2-Aminothiazole-4-yl)-2(1,5-dihydroxy-4-pyridone-2-yl)methoxyiminoacetamido]-3-[1-(2-dimethylaminoethyl)-1H tetrazole-5-yl]thiomethyl-ceph-3-em-4-carboxylic acid

[A] 5-Mercapto-1-(2-dimethylaminoethyl)-1H-tetrazole
NMR($D_2O$)δ; 2.64(6H,s), 3.38(2H,t), 3.51(2H,ABq), 4.23(2H,ABq), 4.72(2H,m), 5.14(1H,d), 5.31(2H,ABq), 5.76(1H,d), 6.73(1H,s), 7.08(1H,s), 7.64(1H,s).

EXAMPLE 8

(6R,7R)-7-[(Z)-2-(2-Aminothiazole-4-yl)2-(1,5-dihydroxy-4-pyridone-2-yl)methoxyiminoacetamido]-3-[1-(2-hydroxyethyl)-1H-tetrazole-5-yl]-thiomethyl-ceph-3-em-4-carboxylic acid

[A] 5-Mercapto-1-(2-hydroxyethyl)-1H-tetrazole
NMR($D_2O$)δ;
3.26(1H,d), 3.72(1H,d), 4.05(2H,m), 4.09(1H,d), 4.40(1H,d), 4.57(2H,m), 5.14(1H,d), 5.30(1H,d), 5.38(1H,d), 5.79(1H,d), 6.89(1H,s), 7.09(1H,s), 7.78(1H,s)

EXAMPLE 9

(6R,7R)-7-[(Z)-2-(2-Aminothiazole-4-yl)-2-(1,5-dihydroxy-4-pyridone-2-yl)methoxyiminoacetamido]-3-(4,5-dihydro-4-methyl 5-oxo-6-hydroxy-1,2,4-triazine-3-yl)thiomethyl-ceph-3-em-4-carboxylic acid

[A] 3-Mercapto-4,5-dihydro-4-methyl-5-oxo-6-hydroxy -1,2,4-triazine
NMR($D_2O$)δ; 3.23(1H,d), 3.49(3H,s), 3.73(1H,d), 3.82(1H,d), 4.54(1H,d), 5.10(1H,d), 5.25(1H,d), 5.37(1H,d), 5.77(1H,d), 6.75(1H,s), 7.08(1H,s), 7.66(1H,s)

EXAMPLE 10

(6R,7R)-7-[(Z)-2-(2-Aminothiazole-4-yl)-2-(1,5-dihydroxy-4-pyridone-2-yl)methoxyiminoacetamido]-3-(2,5-dihydro-2-methyl-5-oxo-6-hydroxy-1,2,4-triazine-3-yl)thiomethyl-ceph-3-em-4-carboxylic acid

[A] 3-Mercapto-2,5-dihydro-2-methyl-5-oxo-6-hydroxy -1,2,4-triazine
NMR($D_2O$)δ; 3.43(2H,ABq), 3.69(3H,s), 4.22(2H,ABq), 5.16(1H,d), 5.33(2H,ABq), 5.82(1H,d), 6.86(1H,s), 7.11(1H,s), 7.74(1H,s)

EXAMPLE 11

(6R,7R)-7-[(Z)-2-(2-Aminothiazole-4-yl)-2-(1,5-dihydroxy-4-pyridone-2-yl)methoxyimianoacetamidol-3-(pyridine-4-yl)thiomethyl ceph-3-em-4-carboxylic acid

[A] 4-Mercaptopyridine
NMR($D_2O$)δ; 3.24(1H,d), 3.65(1H,d), 3.84(1H,d), 4.49(1H,d), 5.04(1H,d), 5.24(1H,d), 5.35(1H,d), 5.74(1H,d), 6.69(1H,s), 7.08(1H,s), 7.37(2H,d), 7.59(1H,s), 8.35(2H,d).

EXAMPLE 12

(6R,7R)-7-[(Z)-2-(2-Aminothiazole-4-yl)-2-(1,5-dihydroxy-4-pyridone-2-yl)methoxyiminoacetamido]-3-(1-cyclopropylpyridinium-4-yl)thiomethyl-ceph-3-em-4-carboxylate

[A] 1-Cyclopropyl-4-thiopyridone
NMR($D_2O$)δ; 1.32(4H,m), 3.46(2H,ABq), 4.12(1H,m), 4.30(2H,ABq), 5.13(1H,d), 5.30(2H,ABq), 5.75(1H,d), 6.74(1H,s), 7.02(1H,s), 7.63(1H,s), 7.81(2H,d), 8.54(2H,d)

EXAMPLE 13

(6R,7R)-7-[(Z)-2-(2-Aminothiazole-4-yl)-2-(1,5-dihydroxy-4-pyridone-2-yl)methoxyiminoacetamido]-3-(2,3-dihydro-3-methyl-2-oxo-6-hydroxy-1,3,5-triazine-4-yl)thiomethyl-ceph-3-em-4-carboxylic acid

[A] 4-Mercapto-2,3-dihydro-3-methyl-2-oxo-6-hydroxy -1,3,5-triazine
NMR($D_2O$)δ; 3.45(3H,s), 3.53(2H,ABq), 4.272H,ABq), 5.22(3H,m), 5.82(1H,d), 6.69(1H,s), 7.10(1H,s), 7.65(1H,s).

EXAMPLE 14

(6R,7R)-7-[(Z)-2-(2-Aminothiazole-4-yl)-2-(1,5-dihydroxy-4-pyridone-2-yl)methoxyiminoacetamido]-3-pyridiniummethyl-ceph-3-em-4-carboxylate (a) 4.41 g of ethyl(Z)-2-(2-tritylaminothiazole -4-yl)-2-(4-diphenylmethyloxy-5-p -methoxybenzyloxypyridine-N-oxid-2-yl)methoxyiminoacetate which is obtained in a manner similar to that in (a) of Example 1 but replacing the allyl(Z)-2-(2-tritylaminothiazole-4-yl)-2-hydroxyiminoacetate by the corresponding ethyl ester compound is dissolved in 30 ml of ethanol and 10 ml of tetrahydrofuran. 10 ml of a 2N sodium hydroxide aqueous solution and 5 ml of water are added thereto, and reacted at room temperature for 4 hours.

The formed crystals are filtered off, washed with a mixed solution of tetrahydrofuran - ethanol - water (1:3:1.5), and suspended in 30 ml of water. With ice cooling, 5 ml of 1N HCl is added, and stirred for 30 minutes. The precipitates are filtered off, washed with water, and then dried to obtain 2.55 g of (Z)-2-(2-tritylaminothiazole-4-yl)-2-(4-diphenylmethyloxo-5-p-methoxybenzyloxypyridine-N-oxid-2-yl)methoxyiminoacetic acid. The spectrum data of this compound are in agreement with those obtained in (b) of Example 1.

(b) 0.87 ml of N,N-dimethylformamide and 1.03 ml of phosphorus oxychloride are added, with ice cooling, to 8.1 ml of dichloromethane, and stirred for an hour. 855 mg of the (Z)-2-(2-tritylaminothiazole-4-yl)-2-(4-diphenylmethyloxoy-5-p-methoxybenzyloxypyridine-N-oxid -2-yl)methoxyiminoacetic acid obtained in (a) is dissolved in 8.5 ml of dichloromethane, then 1 ml of the dichloromethane solution prepared above is added thereto at −15° C., and reacted at the same temperature for an hour. Thereafter, this reaction mixture is added dropwise at −3° C. to a solution obtained beforehand by suspending 720 mg of (6R,7R)-7-amino-3-pyridiniummethyl -ceph-3-em-4-carboxylate dihydrochloride in 12 ml of acetonitrile and adding 1.44 ml of bistrimethylsilyltrifluoroacetamide to dissolve, and then reacted with ice cooling for an hour. After the reaction, 100 ml of dichloromethane is added to the reaction mixture, which is then washed twice with 50 ml portions of 15% aqueous NaCl.

It is dried on anhydrous magnesium sulfate, concentrated, then, the precipitates formed by adding 50 ml of ether are filtered off, washed with ether and dried to obtain 1.15 g of (6R,7R)-7-[(Z)-2-(2-tritylaminothiazole-4-yl)-2-(4-diphenylmethyloxy-5-p -methoxybenzyloxypyridine-N-oxid-2-yl) methoxyiminoacetamido]-3-pyridiniummethyl-ceph-3-em-4-carboxylate hydrochloride.

(c) 600 mg of the 3-pyridiniummethyl compound obtained in (b) is suspended in 1 ml of anisole, 2.25 ml of trichloroacetic acid is added thereto with ice cooling, and reacted for 30 minutes. The reaction mixture is poured into 40 ml of isopropyl ether, the formed precipitates are filtered off, washed with isopropyl ether, and then dried 470 mg of the obtained precipitates are suspended, then neutralized with a saturated sodium dicarbonate aqueous solution with ice cooling to dissolve, and then purified by column chromatography on Diaion HP-20 (eluted with water and 5% aqueous acetone) and column chromatography on Sephadex LH-20 (eluted with 50% aqueous methanol) to obtain 84 mg of the title compound as a sodium salt.

NMR(D$_2$O)δ; 3.27(2H,ABq), 5.21(1H,d), 5.29(2H,ABq), 5.48(2H,ABq), 5.86(1H,d), 6.73(1H,s), 7.06(1H,s), 7.54(1H,s), 8.16(2H,m), 8.64(1H,m), 8.99(2H,d).

EXAMPLE 15

(6R,7R)-7[(Z)-2-(2-Aminothioazole-4-yl)-2-(1,5-dihydroxy -4-pyridone-2-yl)methoxyiminoacetamido]-3-acetoxymethyl-ceph-3-em-4-carboxylic acid (a) 4.04 g of the carboxylic acid obtained in Example 1-(b) and 1.55 g of t-butyl(6R,7R)-7-amino-3-acetoxymethyl-ceph-3-em-4-carboxylate are dissolved in 80 ml of dichloromethane, and cooled to −15° C.

1.53 ml of pyridine and 0.49 ml of phosphorus oxychloride are added thereto, and stirred at −15° C.- −10° C. for 30 minutes. 120 ml of saline is added to the reaction mixture, which is then extracted with 300 ml of ethyl acetate. It is washed twice with saturated NaCl (aqueous solution), once with an NaHCO$_3$ aqueous solution and once with saturated NaCl (aqueous solution). It is dehydrated on magnesium sulfate, concentrated, and the residue is purified by silica gel column chromatography (250 g) (CHCl$_3$:MeOH=30:1) to obtain 3.56 g of t-butyl (6R,7R)-7-[(z)-2-(2-tritylaminothiazole-4-yl)-2-(4-diphenylmethyloxy-5-p-methoxybenzyloxypyridine-N-oxid-2-yl)methoxyiminoacetamido]-3-acetoxymethyl-ceph-3-em-4-carboxylate.

(b) 3.56 g of the compound obtained in (a) is suspended in 3 ml of anisole, then 10 ml of trifluoroacetic acid is added with ice cooling, and reacted at room temperature for 2.5 hours. The reaction mixture is added dropwise to 80 ml of isopropyl ether, the formed precipitates are filtered off, washed with isopropyl ether, and then dried. 2.21 g of the obtained precipitates are suspended in 20 ml of water, and dissolved therein by adjusting the pH to 8 with a saturated sodium bicarbonate aqueous solution. This solution is purified by HP-20 (220 ml). The fraction containing the intended compound is obtained from the elute (water to 5% aqueous acetone), concentrated and freeze dried to obtain 1.06 g of the title compound as a sodium salt.

NMR(D$_2$O)δ; 2.15(3H,s), 3.22(1H,d), 3.63(1H,d), 4.74(1H,d), 4.94(1H,d), 5.19(1H,d), 5.32(1H,d), 5.40(1H,d), 5.84(1H,d), 6.94(1H,s), 7.11(1H,s), 7.82(1H,s).

EXAMPLE 16

(6R,7R)-7-[(Z)-2-(2-Aminothiazole-4-yl)-2-(1,5-dihydroxy -4-pyridone-2-yl)methoxyiminoacetamido]-3-(4-methylthiopyridinium)methyl-ceph-3-em-4-carboxylate (a) 120 mg of the 3-chloromethyl compound (Example 1-(c)) is dissolved in 1 ml of acetone, then 0.5 ml of an acetone solution containing 18 mg of sodium iodide is added, and reacted at room temperature for 45 minutes. The acetone is distilled off, then 1 ml of methylene chloride is added, and the insolubles are removed by filtration to remove the salt. The methylene chloride is distilled off, then 1 ml of acetonitrile and 38 mg of 4-methylthiopyridine are added to the residue, and reacted at room temperature for 1.5 hours with stirring. 0.05 ml of acetic acid and 10 ml of toluene are added to the reaction mixture, and then the solvent is distilled off to dryness. 8 ml of ethyl acetate and 2 ml of isopropyl ether are added to the residue, stirred, and the insolubles are filtered off to obtain 100 mg of p-methoxybenzyl(6R,7R)-7[(Z)-2-(2-tritylaminothiazole-4-yl)-2-(4-diphenylmethyloxy-5-methoxybenzyloxypyridine-N-oxid-2-yl) methoxyiminoacetamido]-3-(4-methylthiopyridinium)methyl-ceph-3-em-4-carboxylate.

(b) 100 mg of the 3-substituted compound obtained in (a) is suspended in 0.07 ml of anisole and 1 ml of trifluoroacetic acid, 0.5 ml of formic acid is added, and stirred at room temperature for an hour. The insolubles are removed by filtration, the remaining solution is added dropwise to 30 ml of isopropyl ether, and the formed precipitates are filtered off Thereafter, they are dissolved in 1 ml of water, neutralized by adding a saturated sodium bicarbonate aqueous solution with ice cooling, and then purified by column chromatography on HP-20 (eluted with 10% aqueous acetone) to obtain 16 mg of the title compound as a sodium salt.

NMR(D$_2$O)δ; 3.24(2H,AB,q), 5.13(1H,d), 5.21(1H,d), 5.22(1H,d), 5.36(1H,d), 5.38(1H,d), 5.83(1H,d), 6.71(1H,s), 7.01(1H,s), 7.54(1H,s), 7.81(2H,d), 8.56(2H,d).

Compounds of the following Examples 17-18 are obtained treating in a manner similar to that in Example 16 except that the 4-methylthiopyridine in (a) of Example 16 is replaced by reagents [A] respectively.

EXAMPLE 17

(6R,7R)-7-[(Z)-2-(2-aminothiazole-4-yl)-2-(1,5-dihydroxy-4-pyridone 2-yl)methoxyiminoacetamido]-3-(4-carbamoylpyridinium)methyl-ceph-3-em-4-carboxylate

[A] isonicotinamido

NMR($D_2O$)$\delta$; 2.94(1H,d), 3.58(1H,d), 5.17(1H,d), 5.34(2H,ABq), 5.40(1H,d), 5.66(1H,d), 5.83(1H,d), 6.76(1H,s), 7.02(1H,s), 7.49(1H,s), 8.43(2H,d), 9.14(2H,d).

EXAMPLE 18

(6R,7R)-7-[(Z)-2-(2-aminothiazole-4-yl)-2-(1,5-dihydroxy -4-pyridone 2-yl)methoxyiminoacetamido]-3-(isoquinolium-2-yl)methyl-ceph-3-em-4-carboxylate

[A] isoquinoline

NMR($D_2O$)$\delta$; 2.94(1H,d), 3.55(1H,d), 5.15(2H,m), 5.32(1H,d), 5.48(1H,d), 5.67(1H,d), 5.83(1H,d), 6.64(1H,s), 7.03(1H,s), 7.37(1H,s), 8.07(1H,m), 8.25(2H,m), 8.45(3H,m), 8.62(1H,d).

EXAMPLE 19

(6R,7R)-7-[(Z)-2-(2-Aminothiazole-4-yl)-2-(1,5-dihydroxy -4-pyridone-2-yl)methoxyiminoacetamido]-3-(4-cyclopropylthiopyridinium)methyl-ceph-3-em-4-carboxylate 200 mg of the sodium salt of (6R,7R)-7-[(Z)-2-(2-aminothiazole-4-yl)-2-(1,5-dihydroxy-4-pyridone-2-yl) methoxyiminoacetamido]-3-acetoxymethyl-ceph-3-em-4-carboxylic acid is dissolved in 1 ml of acetonitile and 1 ml of water, 525 mg of sodium iodide and 160 mg of 4-cyclopropylthiopyridine are added thereto, and, after adjusting the pH to 6.5-7.0 with a 10% phosphoric acid aqueous solution, reacted at 65° C. for 3 hours. After the reaction, 10 ml of acetone is added, and the formed precipitates are filtered off. This is purified by HP-20 column chromatography (eluted with 5% aqueous acetone) and Sephadex LH-20 column chromatography (eluted with 50% aqueous methanol) to obtain 15 mg of the intended title compound as a sodium salt.

NMR($D_2O$)$\delta$; 0.84(2H,bs), 1.35(2H,m), 2.42(1H,m), 3.31(1H,ABq), 5.1-5.5(5H,m), 5.84(1H,d), 6.71(1H,s), 7.02(1H,s), 7.55(1H,s), 7.99(2H,d), 8.56(2H,d).

EXAMPLE 20

(6R,7R)-7-[(Z)-2-(2-Aminothiazole-4-yl)-2-(1,5-dihydroxy -4-pyridone-2-yl)methoxyiminoacetamido]-3-(4-cyclopropylmethylthiopyridinium)-methyl-ceph-3-em-4-carboxylate Procedures similar to those in Example 17 are repeated except that the 4-cyclopropylthiopyridine in Example 19 is replaced by 4-cyclopropylmethylthiopyridine, to obtain the intended title compound as a sodium salt.

NMR($D_2O$)$\delta$; 0.42(2H,m), 0.72(2H,m), 1.24(1H,m), 3.03(2H,d), 3.31(2H,ABq), 5.1 5.4(5H,m), 5.84(1H,d), 6.72(1H,s), 7.04(1H,s), 7.60(1H,s), 7.84(2H,d), 8.56(2H,d).

EXAMPLE 21

(6R,7R)-7-[(Z)-2-(2-Aminothiazole-4-yl)-2-(1,5-dihydroxy-4-pyridone-2-yl)methoxyiminoacetamido]-3-(2,3-cyclopenteno-1-methylpyridinium-4-yl)thiomethyl-ceph-3-em-4-carboxylate (a) 4 g of 1,5-di-p-methoxybenzyloxy-2-hydroxymethyl -4-pyridone is dissolved in 100 ml of dichloromethane, 2.2 ml of thionyl chloride is added dropwise thereto at −10° C., and reacted at the same temperature for an hour and further with ice cooling for 2 hours.

150 ml of a saturated sodium bicarbonate aqueous solution and 50 ml of dichloromethane are added thereto. The dichloromethane layer is dehydrated with anhydrous magnesium sulfate, and concentrated. The formed crystals are washed with dichloromethane to obtain 3.05 g of 1,5-di-p-methoxybenzyloxy-2-chloromethyl-4-pyridone. 2.5 g of this is dissolved in 50 ml of N,N-dimethylformamide, 2.35 g of allyl(Z)-2-(2-tritylaminothiazole-4-yl)-2-hydroxyiminoacetate and 1.66 g of anhydrous potassium carbonate are added, and reacted overnight at room temperature. After the reaction, 150 ml of ethyl acetate is added to the reaction mixture, which is then washed with water and 15% saline, dehydrated on anhydrous magnesium sulfate, and concentrated to about 20 ml. 20 ml of ether is added thereto, and the formed precipitates are filtered off to obtain 3.62 g of allyl(Z)-2-(2-tritylaminothiazole-4-yl)-2-(1,5 di-p-methoxybenzyloxy -4-pyridone-2-yl)methoxyiminoacetate.

NMR(CDCl$_3$)$\delta$; 3.79(3H,s), 3.81(3H,s), 4.72(2H,d), 4.96(2H,s), 4.99(2H,s), 5.09(2H,s), 5.22(1H,d), 5.33(1H,d), 5.86(1H,m), 6.47(1H,s), 6.54(1H,s), 6.8-7.0(5H,m), 7.3(17H,m), 7.19(2H,d).

(b) Using 3.39 g of the allyl ester, procedures similar to those in Example 1-(b) are conducted to obtain 2.65 g of (Z)-2-(2-tritylaminothiazole-4-yl)-2-(1,5-di-p-methoxybenzyloxy-4-pyridone-2-yl)methoxyiminoacetic acid.

1.62 g of this is suspended in 40 ml of dichloromethane, then, 1.08 g of a p-toluenesulfonate salt of p-methoxybenzyl(6R,7R)-7-amino3-chloromethyl -ceph-3-em-4-carboxylate is added, further 0.8 ml of pyridine and 0.2 ml of phosphorus oxychloride are added at −10° C., and reacted for an hour. After the reaction, 80 ml of dichloromethane and 40 ml of 15% saline are added, and the organic layer is washed with 15% saline, dehydrated on anhydrous magnesium sulfate, and concentrated to dryness. This is purified by silica gel column chromatography (chloroform - methanol = 50:1) to obtain 890 mg of p-methoxybenzyl(6R,7R)-7-[(Z)-2-(2-tritylaminothiazole-4-yl)-2-(1,5-di-p-methoxybenzyloxy -4-pyridone-2-yl) methoxyiminoacetamido]-3-chloromethyl -ceph-3-em-4-carboxylate.

NMR(CDCl$_3$)$\delta$; 3.46(2H,ABq), 3.77(3H,s), 3.78(3H,s), 3.79(3H,s), 4.47(2H,ABq), 4.9-5.1(7H,m), 5.20(2H,ABq), 5.79(1H,dd), 6.43(1H,s), 6.78(1H,s), 6.88(6H,m), 6.99(1H,s), 7.17(2H,d), 7.30(20H,m).

(c) 200 mg of the 3-chloromethyl compound obtained in (b) is dissolved in 0.5 ml of dimethylsulfoxide, 36 mg of 1-methylcyclopentano[b]4-thiopyridone is added thereto, and reacted for 1.5 hours. 10 ml of ethyl acetate is added thereto, and the formed precipitates are filtered off. They are suspended 0.14 ml of anisole, 0.43 ml of trifluoroacetic acid is added, and reacted at room temperature for 30 minutes. After the reaction, the reaction mixture is added dropwise to 8 ml of isopropyl ether, and the precipitates are filtered off. They are dried, then suspended in 3 ml of water, 1.1 ml of a saturated sodium bicarbonate aqueous solution is added to dissolve, and the solution is purified by HP-20 column chromatography (eluted with 5% aqueous acetone) to obtain 56 mg of the intended title compound as a sodium salt.

The spectrum data of this compound are in agreement with those obtained in Example 4.

EXAMPLE 22

Injectable preparation

The compound of Example 1 is aseptically allotted into vials so as to give 1000 mg (strength) per vial.

EXAMPLE 23

| Capsules | |
|---|---|
| Compound of Example 1 | 250 parts (strength) |
| Lactose | 60 parts (strength) |
| Magnesium stearate | 5 parts (strength) |

These are uniformly mixed and filled into capsules so as to give 250 mg (strength) per capsule.

EXAMPLE 24

Soft capsules for intrarectal administration

To a uniform base consisting of:

| Olive oil | 160 parts |
|---|---|
| Polyoxyethylene lauryl ether | 10 parts |
| Sodium hexametaphosphate | 5 parts | is added 25 parts (strength) of the compound of Example 1, mixed uniformly and filled into soft capsules for intrarectal administration so as to give 250 mg (strength) per capsule.

EXAMPLE 25

(6R,7R)-7-[(Z)-2-(2-Aminothiazole-4-yl)-2-(1,5-dihydroxy-4-pyridone-2-yl)methoxyiminoacetamido]-3-(1,2,3-thiadiazole-5yl)thiomethyl-ceph-3-em-4-carboxylic acid (a) Using 13.29 g of the 1-diphenylmethyloxy-5-p-methoxybenzyloxy-2-hydroxymethyl-4-pyridone obtained in reference example 4, procedures similar to those in Example 21-(a) and (b) are conducted to obtain 19.05 g of (Z) 2-(2-tritylaminothiazole-4-yl)-2-(1-diphenylmethyloxy-5-p-methoxybenzyloxy-4-pyridone-2-yl) methoxyiminoacetic acid.

NMR(CDCl$_3$)δ; 3.75(3H,s), 4.51(2H,s), 5.08(2H,s), 6.33(1H,s), 6.56(1H,s), 6.67(1H,s), 6.79(2H,d), 7.00(1H,s), 7.09(2H,d), 7.2–7.4(26H,m).

(b) 854 mg of the compound obtained in (a) is dissolved in 20 ml of dichloromethane, and 540 mg of a p-toluenesulfonate salt of p-methoxybenzyl(6R,7R)-7-amino-3-chloromethyl-ceph-3-em-4-carboxylate and 0.4 ml of pyridine are added thereto with ice cooling.

0.1 ml of phosphorus oxychloride is added dropwise thereto at −10° C. to −15° C., and reacted at the same temperature for 30 minutes.

After the reaction, 20 ml of saturated NaCl and 40 ml of ethyl acetate are added, and the organic layer is washed twice with saturated saline. It is dried on magnesium sulfate, and concentrated to dryness under reduced pressure to obtain 1.58 g of a crude powder of p-methoxybenzyl(6R,7R)-7-[(Z)-2-(2-tritylaminothiazole-4-yl)-2-(1-diphenylmethyloxy-5-p-methoxybenzyloxy-4-pyridone-2-yl)-methoxyiminoacetamido]-3-chloromethyl-ceph-3-em-4-carboxylate.

(c) The obtained chloromethyl compound is dissolved in 2 ml of dimethylsulfoxide, 175 mg of a sodium salt of 5-mercapto-1,2,3-thiadiazole is added, and reacted at room temperature for an hour. Thereafter, procedures similar to those in Example 1-(d) are conducted to obtain 203 mg of the intended title compound as a sodium salt.

The NMR data of the obtained compound are in agreement with those in Example 6.

Compounds of the following Examples 26–46 are obtained by treating in a manner similar to that in Example 23 except that the 5-mercapto-1,2,3-thiadiazole in (c) of Example 25 is replaced by reagents [A] respectively.

EXAMPLE 26

(6R,7R)-7-[(Z)-2-(2-Aminothiazole-4-yl)-2-(1,5-dihydroxy-4-pyridone-2-yl)methoxyiminoacetamido]-3-(4-methyloxazole-2-yl)thiomethyl-ceph-3-em-4-carboxylic acid

[A] 2 Mercapto-4-methyloxazole
NMR(D$_2$O)δ; 2.13(3H,s), 3.47(2H,ABq), 4.18(2H,ABq), 5.08(1H,d), 5.30(2H,ABq), 5.74(1H,d), 6.72(1H,s), 7.07(1H,s), 7.64(1H,s).

EXAMPLE 27

(6R,7R)-7-[(Z)-2-(2-Aminothiazole-4-yl)-2-(1,5-dihydroxy
-4-pyridone-2-yl)methoxyiminoacetamido]-3-(benzothiazole-2-yl)thiomethyl-ceph-3-em-4-carboxylic acid

[A] 2-Mercaptobenzothiazole
NMR(D$_2$O)δ; 3.37(2H,ABq), 4.32(2H,ABq), 4.94(1H,d), 5.25(2H,ABq), 5.72(1H,d), 6.67(1H,s), 7.04(1H,s), 7.42(1H,t), 7.54(1H,t), 7.57(1H,s), 7.86(1H,d), 7.91(1H,d).

EXAMPLE 28

(6R,7R)-7-[(Z)-2-(2-Aminothiazole-4-yl)-2-(1,5-dihydroxy-4-pyridone-2-yl)methoxyiminoacetamido]-3-(1,3,4-thiadiazole-2-yl)thiomethyl-ceph-3-em-4-carboxylic acid

[A] 2-Mercapto-1,3,4-thiadiazole
NMR(D$_2$O)δ; 3.49(2H,ABq), 4.28(2H,ABq), 5.10(1H,d), 5.29(2H,ABa), 5.75(1H,d), 6.72(1H,s), 7.07(1H,s), 7.65(1H,s), 9.43(1H,s).

EXAMPLE 29

(6R,7R)-7-[(Z)-2-(2-Aminothiazole-4-yl)-2-(1,5-dihydroxy-4-pyridone-2-yl)methoxyiminoacetamido]-3-(4-methyl -1,2,3-thiadiazole-5-yl)
thiomethyl-ceph-3-em-4-carboxylic acid

[A] 5-Mercapto-4-methyl 1,2,3-thiadiazole
NMR(D$_2$O)δ; 2.67(3H,s), 3.23(1H,d), 3.72(1H,d), 3.79(1H,d), 4.34(1H,d), 5.12(1H,d), 5.24(1H,d), 5.36(1H,d), 5.74(1H,d), 6.72(1H,s), 7.08(1H,s), 7.62(1H,s).

EXAMPLE 30

(6R,7R)-7-[(Z)-2-(2-Aminothiazole-4-yl)-2-(1,5-dihydroxy-4-pyridone-2-yl)methoxyiminoacetamido]-3-(4-hydroxyphenyl)thiomethyl-ceph-3-em-4-carboxylic acid

[A] 4-hydroxythiophenol
NMR(D$_2$O)δ; 3.14(1H,d), 3.44(1H,d), 3.66(1H,d), 4.37(1H,d), 4.98(1H,d), 5.26(1H,d), 5.33(1H,d), 5.67(1H,d), 6.69(1H,s), 6.84(2H,d), 7.07(1H,s), 7.37(2H,d), 7.60(1H,s).

EXAMPLE 31

(6R,7R)-7-[(Z)-2-(2-Aminothiazole-4-yl)-2-(1,5-dihydroxy-4-pyridone-2-yl)methoxyiminoacetamido]-3-(4-phlorophenyl)thiomethyl-ceph-3-em-4-carboxylic acid

[A] 4-phlorothiophenol
NMR(D$_2$O)δ; 3.15(1H,d), 3.52(1H,d), 3.70(1H,d), 4.44(1H,d), 4.97(1H,d), 5.23(1H,d), 5.34(1H,d), 5.65(1H,d), 6.71(1H,s), 7.10(3H,m), 7.45(2H,m), 7.63(1H,s).

EXAMPLE 32

(6R,7R)-7-[(Z)-2-(2-Aminothiazole-4-yl)-2-(1,5-dihydroxy-4-pyridone-2-yl)methoxyiminoacetamido]-3-(4-carbamoylthiazole-5-yl)thiomethyl-ceph-3-em-4-carboxylic acid

[A] 5-mercapto-4-carbamoylthiazole
NMR(D$_2$O)δ; 3.20(1H,d), 3.73(1H,d), 3.74(1H,d), 4.45(1H,d), 5.06(1H,d), 5.29(2H,ABq), 5.74(1H,d), 6.71(1H,s), 7.07(1H,s), 7.62(1H,s), 8.92(1H,s)

EXAMPLE 33

(6R,7R)-7-[(Z)-2-(2-Aminothiazole-4-yl)-2-(1,5-dihydroxy-4-pyridone-2-yl)methoxyiminoacetamido-3-(thiazole-5-yl)thiomethyl-ceph-3-em-4-carboxylic acid

[A] 5-mercaptothiazole
NMR(D$_2$O)δ; 3.20(1H,d), 3.52(1H,d), 3.80(1H,d), 4.33(1H,d), 5.13(1H,d), 5.31(2H,ABq), 5.70(1H,d), 6.73(1H,s), 7.08(1H,s), 7.62(1H,s), 7.86(1H,s) 9.02(1H,s).

EXAMPLE 34

(6R,7R)-7-[(Z)-2-(2-Aminothiazole-4-yl)-2-(1,5-dihydroxy-4-pyridone-2yl)methoxyiminoacetamido]-3-(2-methyl -1,3,4-thiadiazole-5-yl)thiomethyl-ceph-3-em-4-carboxylic acid

[A] 5-mercapto-2-methyl-1,3,4-thiadiazole
NMR(D$_2$O)δ; 2.75(3H,s), 3.23(1H,d), 3.74(1H,d), 3.94(1H,d), 4.50(1H,d), 5.10(1H,d), 5.31(2H,ABq), 5 76(1H,d), 6.72(1H,s), 7.08(1H,s), 7.63(1H,s).

EXAMPLE 35

(6R,7R)-7-[(Z)-2-(2-Aminothiazole-4-yl)-2-(1,5-dihydroxy-4-pyridone-2-yl)methoxyiminoacetamido]-3-(4-ethoxycarbonyl-1,2,3-thiadiazole-5-yl)thiomethyl-ceph-3-em -4-carboxylic acid

[A] 5-mercapto-4-ethoxycarbonyl-1,2,3-thiadiazole
NMR(D$_2$O)δ; 1.43(3H,t), 3.23(1H,d), 3.58(1H,d), 4.11(1H,d), 4.41(1H,d), 4.48(2H,q), 5.11(1H,d), 5.27(2H,ABq), 5.80(1H,d), 6.71(1H,s), 7.01(1H,s), 7.59(1H,s)

EXAMPLE 36

(6R,7R)-7-[(Z)-2-(2-Aminothiazole-4-yl)-2-(1,5-dihydroxy-4-pyridone-2-yl)methoxyiminoacetamido]-3-(4-carbamoyl-1,2,3-thiadiazole-5-yl)thiomethyl-ceph-3-em-4-carboxylic acid

[A] 5-mercapto-4-carbamoyl-1,2,3-thiadiazole
NMR(D$_2$O)δ; 3.21(1H,d), 3.60(1H,d), 4.07(1H,d), 4.38(1H,d), 5.10(1H,d), 5.26(2H,ABq), 5.78(1H,d), 6.70(1H,s), 7.02(1H,a), 7.58(1H,s).

EXAMPLE 37

(6R,7R)-7-[(Z)-2-(2-Aminothiazole-4-yl)-2-(1,5-dihydroxy-4-pyridone-2-yl)methoxyiminoacetamido]-3-(2-ethoxy-1,3,4-thiadiazole-5-yl)thiomethyl-ceph-3-em-4-carboxylic acid

[A] 5-mercapto-2-ethoxy-1,3,4-thiadiazole
NMR(D$_2$O)δ; 1.46(3H,t), 3.22(1H,d), 3.76(1H,d), 3.83(1H,d), 4.44(1H,d), 4,54(2H,q), 5.12(1H,d), 5.29(2H,ABq), 5.74(1H,d), 6.71(1H,s), 7.07(1H,s), 7.63(1H,s).

EXAMPLE 38

(6R,7R)-7-[(Z)-2-(2-Aminothiazole-4-yl)-2-(1,5-dihydroxy-4-pyridone-2-yl)methoxyiminoacetamido]-3-(2-ethylthio-1,3,4-thiadiazole-5-yl)thiomethyl-ceph-3-em-4-carboxylic acid

[A] 5-mercapto-2-ethylthio-1,3,4-thiadiazole
NMR(D$_2$O)δ; 1.41(3H,t), 3.22(1H,d), 3.26(2H,q), 3.72(1H,d), 3.95(1H,d), 4.50(1H,d), 5.10(1H,d), 5.28(2H,ABq), 5.74(1H,d), 6.71(1H,s), 7.07(1H,a), 7.62(1H,s).

EXAMPLE 39

(6R,7R)-7-[(Z)-2-(2-Aminothiazole-4-yl)-2-(1,5-dihydroxy-4-pyridone-2-yl)methoxyiminoacetamido]-3-(2-ethoxycarbonyl -1,3,4-thiadiazole-5-yl)thiomethyl-ceph-3-em-4-carboxylic acid

[A] 5-mercapto-2-ethoxycarbonyl-1,3,4-thiadiazole
NMR(D$_2$O)δ: 1.41(3H,t), 3.47(2H,ABq), 4.35(2H,ABq), 4.50(2H,q), 5.12(1H,d), 5.28(1H,ABq), 5.77(1H,d), 6.72(1H,s), 7.04(1H,s), 7.63(1H,s).

EXAMPLE 40

(6R,7R)-7-[(Z)-2-(2-Aminothiazole-4-vl)-2-(1,5-dihydroxy-4-pyridone-2-yl)methoxyiminoacetamido]-3-(2-carbamoyl-1,3,4-thiadiazole-5-yl)thiomethyl-ceph-3-em-4-carboxylic acid

[A] 5-mercapto-2-carbamoyl-1,3,4-thiadiazole
NMR(D$_2$O)δ; 3.48(2H,ABq), 4.33(2H,ABq), 5.11(1H,d), 5.28(2H,ABq), 5.76(1H,d), 6.70(1H,s), 7.06(1H,s), 7.60(1H,s).

EXAMPLE 41

(6R,7R)-7-[(Z)-2-(2-Aminothiazole-4-yl)-2-(1,5-dihydroxy-4-pyridone-2-yl)methoxyiminoacetamido]-3-(4-ethoxycarbonylthiazole-5-yl)thiomethyl-ceph-3-em-4-carboxylic acid

[A] 5-mercapto-4-ethoxycarbonylthiazole
NMR(D$_2$O)δ; 1.45(3H,t), 3.28(1H,d), 3.72(1H,d), 3.90(1H,d), 4.47(2H,q), 4.57(1H,d), 5.10(1H,d), 5.32(2H,ABq), 5.78(1H,d), 6.72(1H,s), 7.10(1H,s), 7.63(1H,s), 8.93(1H,s).

EXAMPLE 42

(6R,7R)-7-[(Z)-2-(2-Aminothiazole-4-yl)-2-(1,5-dihydroxy-4-pyridone-2-yl)methoxyiminoacetamido]-3-(1,2,4-thiadiazole-5-yl)thiomethyl-ceph-3-em-4-carboxylic acid

[A] 5-mercapto-1,2,4-thiadiazole
NMR($D_2O$)$\delta$; 3.31(1H,d), 3.77(1H,d), 4.20(1H,d), 4.67(1H,d), 5.16(1H,d), 5.34(2H,ABq), 5.83(1H,d), 6.75(1H,s), 7.13(1H,s), 7.65(1H,s), 8.66(1H,s).

EXAMPLE 43

(6R,7R)-7-[(Z)-2-(2-Aminothiazole-4-yl)-2-(1,5-dihydroxy-4-pyridone-2-yl)methoxyiminoacetamido]-3-(3-methyl-1,2,4-thiadiazole-5-yl)thiomethyl-ceph-3-em-4-carboxylic acid

[A] 5-mercapto-3-methyl-1,2,4-thiadiazole
NMR($D_2O$)$\delta$; 2.63(3H,s), 3.29(1H,d), 3.72(1H,d), 4.14(1H,d), 4.61(1H,d), 5.16(1H,d), 5.34(2H,ABq), 5.82(1H,d), 6.77(1H,s), 7.11(1H,s), 7.67(1H,s).

EXAMPLE 44

(6R,7R)-7-[(Z)-2-(2-Aminothiazole-4-yl)-2-(1,5-dihydroxy-4-pyridone-2-yl)methoxyiminoacetamido]-3-(4-phenylthiazole-2-yl)thiomethyl-ceph-3-em-4-carboxylic acid

[A] 2-Mercapto-4-phenylthiazole
NMR($D_2O$)$\delta$; 3.43(2H,ABq), 4.22(2H,ABq), 5.00(1H,d), 5.28(2H,ABq), 5.72(1H,d), 6.69(1H,s), 7.06(1H,s), 7.47–7.54(3H,m), 7.62(1H,s), 7.78(1H,s), 7.86(2H,d),

EXAMPLE 45

(6R,7R)-7-[(Z)-2-(2-Aminothiazole-4-yl)-2-(1,5-dihydroxy-4-pyridone-2-yl)methoxyiminoacetamido]-3-(thiazole-2-yl)thimethyl-ceph-3-em-4-carboxylic acid

[A] 2-Mercaptothiazole
NMR($D_2O$)$\delta$; 3.50(2H,ABq), 4.19(2H,ABq), 5.09(1H,d), 5.31(2H,ABq), 5.74(1H,d), 6.73(1H,s), 7.09(1H,s), 7.34(1H,s), 7.64(1H,s), 7.81(1H,s).

EXAMPLE 46

(6R,7R)-7-[(Z)-2-(2-Aminothiazole-4-yl)-2-(1,5-dihydroxy-4-pyridone-2-yl)methoxyiminoacetamido]-3-(3,4-dihydro-4-methyl-1,1,3-trioxo-2H-1,2,4,6-thiatriazine-5-yl)thiomethyl-ceph-3-em-4-carboxylic acid

[A] 3,4,5,6-Tetrahydro-4-methyl-1,1,3-trioxo-2H-1,2,4,6-thiatriazine-5-thione
NMR($D_2O$)$\delta$; 3.41(3H,s), 3.51(2H,ABq), 4.12(2H,ABq), 5.17(1H,d), 5.31(2H,ABq), 5.81(1H,d), 6.75(1H,s), 7.09(1H,s), 7.68(1H,s).

EXAMPLE 47

(6R,7R)-7-[(Z)-2-(2-Aminothiazole-4-yl)-2-(1,5-dihydroxy-4-pyridone-2-yl)methoxyiminoacetamido]-3-methyl-ceph-3-em-4-carboxylic acid (a) (Z)-2-(2-Tritylaminothiazole-4-yl)-2-(1-diphenylmethyloxy-5-p-methoxybenzyloxy-4-pyridone-2-yl) methoxyiminoacetic acid (427 mg) and t-butyl(6R,7R)-7-amino-3-methyl-ceph-3-em-4-carboxylate (135 mg) are dissolved in methylene chloride (10 ml), and cooled to − 10° C. Pyridine (0.17 ml) and then phosphorus oxychloride (52 μl) are added to this solution, and stirred at −10° C. to −5° C. for 45 minutes. Saturated NaCl (aqueous solution) is added to the reaction mixture, which is then extracted with ethyl acetate. The ethyl acetate layer is washed with saturated NaCl (aqueous solution), a saturated sodium bicarbonate aqueous solution, and saturated NaCl (aqueous solution) successively, dehydrated on magnesium sulfate, and the ethyl acetate is distilled off under reduced pressure. The residue is subjected to column chromatography on silica gel (50 g) and eluted with $CHCl_3$:MeOH (30:1) to obtain 276 mg of t-butyl (6R,7R)-7-[(Z)-2-(2-tritylaminothiazole-4-yl)-2-(1-diphenylmethyloxy-5-p-methoxybenzyloxy-4-pyridone-2-yl)methoxyiminoacetamido]-3-methyl-ceph-3-em-4-carboxylate.

(b) The compound obtained in (a) (276 mg) is suspended in anisole (0.25 ml), trifluoroacetic acid (1 ml) is added with ice cooling, and stirred at room temperature for 2.5 hours. The reaction mixture is added to diisopropyl ether (30 ml), and the precipitates are filtered off. After drying, they are suspended in water (10 ml), and the pH is adjusted to 8.2 with a saturated sodium bicarbonate aqueous solution to dissolve. The solution is purified by HP-20 (100 ml, eluted with water) and LH-20 (50 ml), the fraction containing the intended compound is freeze dried to obtain 41 mg of the intended title compound as a sodium salt.

NMR($D_2O$)$\delta$; 1,93(3H,s), 3.05(1H,d), 3.53(1H,d), 5.12(1H,d), 5.27(1H,d), 5.36(1H,d), 5.74(1H,d), 6.78(1H,s), 7.09(1H,s), 7.69(1H,s).

EXAMPLE 48

(6R,7R)-7-[(Z)-2-(2-Aminothiazole-4-yl)-2-(1,5-dihydroxy-4-pyridone-2-yl)methoxyiminoacetamido]-3-hydroxymethyl-ceph-3-em-4-carboxylic acid Sodium(6R,7R)-7-[(Z)-2-(2-aminothiazole-4-yl)-2-(1,5-dihydroxy-4-pyridone-2-yl)methoxyiminoacetamido]-3-acetoxymethyl-ceph-3-em-4-carboxylate (100 mg) is dissolved in 50% aqueous methanol (2 ml), and cooled to −20° C. 1N-NaOH (0.2 ml) is added and stirred at −20° C. to −25° C. for 30 minutes. 1N-NaOH (0.2 ml) is further added, and stirred at the same temperature for an hour. The pH is adjusted to 6 with 1N-HCl, and the methanol is distilled off under reduced pressure. The pH is adjusted to 8 with a saturated sodium bicarbonate aqueous solution, and the solution is purified by HP-20 (70 ml, eluted with water) and LH-20 (50% aqueous methanol) to obtain 54 mg of the intended title compound as a sodium salt.

NMR($D_2O$)$\delta$; 3.27(1H,d), 3.59(1H,d), 4.27(1H,d), 4.31(1H,d), 5.15(1H,d), 5.25(1H,d), 5.35(1H,s), 5.78(1H,d), 6.73(1H,s), 7.08(1H,s), 7.64(1H,s).

Compounds of the following Examples 49–50 are obtained treating in a manner similar to that in Example 53 except that the 5-mercapto-1,2,3-thiazole in (d) of Example 53 is replaced by reagents [A] respectively.

EXAMPLE 49

(6R,7R)-7-{(Z)-2-(2-aminothiazole-4-yl)-2-[(RS)-1-(1,5-dihydroxy-4-pyridone-2-yl)ethoxyimono]acetamido}-3-[1-(2-dimethylaminoethyl)-1H-tetrazole-5-yl]thiomethyl-ceph-3-em-4-carboxylic acid

[A] 5-mercapto-1-(2-dimethylaminoethyl)-1H-tetrazole
NMR($D_2O$)$\delta$; 1.61(3H,t), 2,40(3H,s), 2.41(3H,s), 3.10(2H,m), 4.13(1/2H,d), 4.15(1/2H,d), 4.38(1/2H,d), 4.41(1/2H,d), 4.60(2H,m), 5.15(1/2H,d), 5.26(1/2H,d), 5.80(2H,m), 6.63(1/2H,s), 6.73(1/2H,s), 7.04(1H,s), 7.59(1H,s).

EXAMPLE 50

(6R,7R)-7-{(Z)-2-(2-aminothiazole-4-yl)-2-[(RS)-1-(1,5-dihydroxy-4-pyridone-2-yl)ethoxyimono]acetamido}-3-(1,2,4-thiadiazole-5-yl)thiomethyl-ceph-3-em-4-carboxylic acid

[A] 5-mercapto-1,2,4-thiadiazole

NMR($D_2O$)δ; 1.61(3H,t), 3,28(1/2H,d), 3.49(1/2H,d), 3.70(1/2H,d), 3.80(1/2H,d), 4.13(1/2H,d), 4.17(1/2H,d), 4.63(1/2H,d), 4.67(1/2H,d), 5.12(1/2H,d), 5.23(1/2H,d), 5.8 5.9(2H,m), 6.64(1/2H,s), 6.76(1/2H,s), 7.03(lH,s), 7.62(1/2H,s), 7.63(1/2H,s), 8.60(lH,s),

EXAMPLE 51

(6R,7R)-7-[(Z)-2-(2-Aminothiazole-4-yl)-2-(1,5-dihydroxy-4-pyridone-2-yl)methoxyiminoacetamido]-3-vinyl-ceph-3-em-4-carboxylic acid (a) Procedures similar to those in Example 47, (a) are repeated except that the t-butyl(6R,7R)-7-amino -3-methyl-ceph-3-em-4-carboxylate is replaced by 198 mg of diphenylmethyl(6R,7R)-7-amino-3-vinyl-ceph-3-em-4-carboxylate to obtain 400 mg of diphenylmethyl(6R,7R)-7-[(Z) -2-(2-tritylaminothiazole-4-yl)-2-(4-diphenylmethyloxy-5-p-methoxybenzyloxypyridine-N-oxid-2-yl)-methoxyiminoacetamido]-3-vinyl-ceph-3-em-4-carboxylate.

(b) 380 mg of the compound obtained in (a) is dissolved in 0.41 ml of anisole, 1.22 ml of trifluoroacetic acid is added with ice cooling, and reacted at the same temperature for an hour. The reaction mixture is added dropwise to 30 ml of isopropyl ether, the formed precipitates are filtered off, washed with isopropyl ether and dried. 170 mg of the obtained precipitates are suspended in 3 ml of water, and, after dissolving by adding a saturated sodium bicarbonate aqueous solution to pH 7.9, purified by column chromatography on Diaion HP-20 (eluted with $H_2O$ - 5% aqueous acetone) and column chromatography on Sephadex LH-20 (eluted with 50% aqueous MeOH) to obtain 80 mg of the intended title compound.

NMR($D_2O$)δ; 3.54(2H,s), 5.18(lH,d), 5.29(lH,d), 5.30(2H,ABq), 5.47(lH,d), 5.79(lH,d), 6.71(lH,s), 6.75(lH,dd), 7.09(lH,s), 7.62(lH,s).

EXAMPLE 52

(6R,7R)-7-[(Z)-2-(2-Aminothiazole-4-yl)-2-(1,5-dihydroxy-4-pyridone-2-yl)methoxyiminoacetamido]-3-azidomethyl-ceph-3-em-4-carboxylic acid 58 mg of sodium(6R,7R)-[(Z)-2-(2-aminothiazole-4-yl)-2-(1,5-dihydroxy-4-pyridone-2yl)methoxyiminoacetamido]-3-acetoxymethyl-ceph-3-em-4-carboxylate is dissolved in 1 ml of water, 20 mg of sodium azide is added, and, after adjusting the pH to 6.5–6.8 with a saturated sodium bicarbonate aqueous solution, reacted at 60°–65° C. for 4.5 hours. The reaction mixture is directly purified by column chromatography on HP-20 (eluted with water) and LH-20 (50% aqueous methanol) to obtain the intended title compound as a sodium salt.

NMR($D_2O$)δ;
3.42(2H,ABq), 4.11(2H,ABq), 5.17(lH,d), 5.30(2H,ABq), 5.80(lH,d), 6.70(lH,s), 7.08(lH,s), 7.61(lH,s).

EXAMPLE 53

(6R,7R)-7-{(Z)-2-(2-Aminothiazole-4-yl)-2-[(RS)-1-(1,5-dihydroxy-4-pyridone-2-yl)ethoxyimino]acetamido}-3-(1,2,3-thiadiazole-5-yl]-thiomethyl-ceph-3-em-4-carboxylic acid (a) 2 g of 1,5-di-p-methoxybenzyloxy-2-hydroxymethyl-4-pyridone is dissolved in 50 ml of acetonitrile, 10 g of active manganese dioxide is added, and reacted at 50° C. for 3.5 hours.

After the reaction, the manganese dioxide is removed by filtration, then washed with acetonitrile, and the filtrate is concentrated under reduced pressure. The residue is dissolved in 100 ml of dichloromethane, washed with water, dried on anhydrous magnesium sulfate, and concentrated under reduced pressure. This is purified by silica gel column chromatography (chloroform — methanol=50:1) to obtain 1.15 g of 2-formyl-1,5-di-p -methoxybenzyloxy-4-pyridone.

NMR($CDCl_3$)δ; 3.81(3H,s), 3.82(3H,s), 5.00(2H,s), 5.08(2H,s), 6.72(lH,s), 6.84(2H,d), 6.89(2H,d), 7.05(2H,d), 7.10(lH,s), 7.31(2H,d), 9.60(lH,s).

(b) 1.09 g of the formyl compound is suspended in 20 ml of THF, 7.5 ml of a 1M tetrahydrofuran solution of methylmagnesium bromide with ice cooling, and reacted at the same temperature for an hour. 30 ml of a dilute ammonium chloride aqueous solution is added to the reaction mixture, which is then extracted with 120 ml of ethyl acetate. The extract is washed with water, dried on anhydrous magnesium sulfate, and concentrated under reduced pressure. The residue is purified by silica gel column chromatography (chloroform:methanol=50:1) to obtain 530 mg of 1,5-di-p-methoxybenzyloxy-2-[(RS)-1-hydroxyethyl]-4-pyridone.

NMR($CDCl_3$)δ; 1.44(3H,d), 3.79(3H,s), 3.80(3H,s), 4.87(2H,ABq), 4.95(lH,q), 5.04(2H,ABq), 6.54(lH,s), 6.80(2H,d), 6.90(2H,d), 6.99(lH,s), 7.21(2H,d), 7.25(2H,d).

(c) Using 495 mg of the alcohol compound obtained in (b), procedures similar to those in (a) and (b) of Example 19 are conducted to obtain 320 mg of p -methoxybenzyl(6R,7R)-7-{(Z)-2-(2-tritylaminothiazole-4-yl)-2-[(RS)-1-(1,5-di-p-methoxybenzyloxy-4-pyridone-2-yl ethoxyimino]acetamido}-3-chloromethyl-ceph-3-em-4-carboxylate.

(d) 150 mg of the obtained chloromethyl compound is dissolved in 0.4 ml of dimethylsulfoxide, 30 mg of 5-mercapto-1,2,3-thiadiazole is added, and reacted at room temperature for an hour. Thereafter, procedures similar to those in Example 1-(d) are conducted to obtain 51 mg of the intended title compound as a sodium salt.

NMR($D_2O$)δ; 1.57(3/2H,d), 1.62(3/2H,d), 3.48(lH,ABq), 3.60(lH,ABq), 4.11(lH,ABq), 4.16(lH,ABq), 5.12(1/2H,d), 5.21(1/2H,d), 5.75(1/2H,d), 5.78(1/2H,d), 5.81(lH,q), 6.61(1/2H,s), 6.71(1/2H,s), 7/02(1/2H,s), 7/04(1/2H,s), 7.54(1/2H,s), 7.56(1/2H,s), 8.72(lH,s).

EXAMPLE 54

(6R,7R)-7-{(Z)-2-(2-Aminothiazole-4-yl)-2-[(RS)-1-(1,5-dihydroxy-4-pyridone-2-yl)propoxyimino]acetamido}-3-(1,2,3 -thiadiazole-5-yl)-thiomethyl-ceph-3-em-4-carboxylic acid The title compound is obtained treating in a manner similar to that in Example 53 except that the methylmagnesium bromide in (b) of Example 53 is replace by the ethylmagnesium bromide.

NMR(D₂O)δ; 1.03(3H,t), 2.00(2H,m), 3.40(1/2H,d), 3.51(1/2H,d), 3.77(1/2H,d), 3.83(1/2H,d), 3.97(1/2H,d), 4.01(1/2H,d), 4.43(1/2H,d), 4.46(1/2H,d) 5.20(1/2H,d), 5.27(1/2H,d), 5.68(1H,m), 5.83(1H,d), 6.61(1/2H,s), 6.72(1/2H,s), 7.08(1H,s), 7.62(1H,s), 8.77(1H,s).

EXAMPLE 55

(6R,7R)-7-{(Z)-2-(2-Aminothiazole-4-yl)-2-[(RS)-1-phenyl-1-(1,5-dihydroxy-4-pyridone-2yl)methoxyimono]acetamido}-3-(1,2,3-thiadiazole-5-yl)-thiomethyl-ceph-3-em-4-carboxylic acid The title compound obtained treating in a manner similar to that in Example 53 except that the methylmagnesium bromide in (b) of Example 53 is replaced by the phenylmagnesium bromide.

NMR(D₂O)δ; 3.10(1/2H,d), 3.15(1/2H,d), 3.51(1/2H,d), 3.64(1/2H,d), 3.97(1/2H,d), 4.02(1/2H,d), 4.25(1/2H,d), 4.31(1/2H,d), 5.07(1/2H,d), 5.12(1/2H,d), 5.68(1/2H,d), 5.73(1/2H,d), 6.68(1/2H,s), 6.76(1/2H,s), 6.82(1/2H,s), 6.95(1/2H,s), 7.11(1/2H,s), 7.12(1/2H,s), 7.40(5H,s), 7.77(1/2H,s), 7.82(1/2H,s), 8.74(1/2H,s), 8.75(1/2H,s).

TEST EXAMPLE

The compounds (I) of this invention or their salts are novel compounds and exhibit great antibacterial activity which inhibits the growth of pathogenic microorganisms in a wide range covering Gram positive and Gram negative microorganisms. In order to demonstrate the utility of the compounds (I) of this invention, the antibacterial activity values measured on representative ones of the compounds (I) are shown in Table 1.

isms including Pseudomonas aeruginosa and further have characteristics of being excellent in solubility in water which is an important requirement for using in injections.

As the result of an acute toxicity test on the compounds of this invention using mice, LD50 is 2 g/kg or higher and thus low in toxicity.

What is claimed is:

1. A cephalosporin compound of the formula (1):

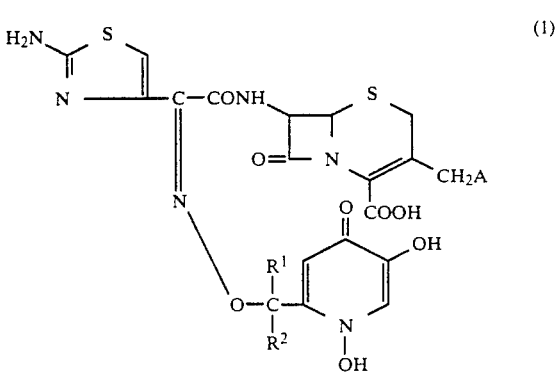

wherein $R^1$ and $R^2$ may be the same or different and are a hydrogen atom, lower alkyl group of 1–5 carbon atoms, or a phenyl group; and A is (1) a hydrogen atom, (2) a hydroxyl group, (3) an azido group, (4) an acetoxy group, (5) a pyridinium group, which may be substituted by a straight-chain, a branched-chain or a cyclic alkylthio group having 1–5 carbon atoms or a carbamoyl group, or (6) an isoquinolinium-2-yl group, or a pharmacologically acceptable salt thereof.

2. A compound according to claim 1, which is (6R,7R)-7-[(Z)-2-(2-aminothiazol-4-yl)-2-(1,5-dihydroxy-4-pyridon-2-yl) methoxyiminoacetamido]-3-pyridiniummethyl-ceph-3-em-4-carboxylate.

TABLE 1

| | | Minimum Growth Inhibitory Concentration | | | | | | | |
|---|---|---|---|---|---|---|---|---|---|
| | | Example 1 | Example 3 | Example 4 | Example 6 | Example 9 | Example 14 | A | B |
| Staphylococcus aureus | 209P JC-1 | 3.13 | 3.13 | 3.13 | 1.56 | 6.25 | 6.25 | 3.13 | 3.13 |
| " | Smith (1) | 3.13 | 6.25 | 6.25 | 3.13 | 12.5 | 6.25 | 3.13 | 3.13 |
| Bacillus subtilis | ATCC6633 | 12.5 | 12.5 | 12.5 | 3.13 | 12.5 | 12.5 | 1.56 | 6.25 |
| Escherichia coli | No. 29 | 0.05 | 0.05 | <0.025 | 0.05 | <0.025 | 0.10 | 0.20 | 0.20 |
| " | No. 255 | 0.10 | 0.20 | 0.20 | 1.56 | 0.20 | 0.78 | 1.56 | 12.5 |
| Klebsiella pneumoniae | GN-69 | <0.025 | 0.05 | 0.10 | 0.05 | <0.025 | 0.10 | 0.20 | 0.10 |
| Proteus vulgaris | GN-76 | 0.05 | 0.05 | <0.025 | <0.025 | <0.025 | 0.20 | 0.20 | 0.05 |
| Proteus rettgeri | GN-624 | 0.10 | 0.10 | 0.20 | 1.56 | 0.20 | 3.13 | 12.5 | 0.39 |
| Citrobacter freundii | GN-346 | 12.5 | 6.25 | 1.56 | 6.25 | 3.13 | 6.25 | 25 | 50 |
| Enterobacter cloacae | GN-471 | 1.56 | 1.56 | 0.78 | 6.25 | 3.13 | 3.13 | 3.13 | 3.13 |
| Serratia marcescens | No. 1 | 0.05 | 0.10 | 0.10 | 0.05 | 0.05 | 0.10 | 0.20 | <0.025 |
| Pseudomonas aeruginosa | M-0148 | 0.20 | 0.20 | 0.10 | 0.20 | 0.39 | 0.78 | 25 | 3.13 |
| " | E-2 | 0.05 | 0.05 | 0.10 | 0.05 | 0.05 | 0.10 | 3.13 | 1.56 |
| " | IAM-1007 | 0.10 | 0.10 | 0.10 | 0.20 | 0.39 | 0.39 | 3.13 | 1.56 |
| Pseudomonase cepacia | M-0527 | <0.025 | <0.025 | <0.025 | <0.025 | <0.025 | <0.025 | 0.39 | 0.78 |

A: (6R,7R)-7-[(Z)-2-(2-Aminothiazole-4-yl)-2-(5-hydroxy-4-pyridone-2-yl)methoxyiminoacetamido]-3-pyridinium-methyl-ceph-3-em-4-carboxylate
B: Ceftazidime The compounds having a (Z)-2-(2-aminothiazole-4-yl)-2-(1,5-dihydroxy-4-pyridone-2-yl)alkoxyimino group on the 7-position, as compared with the 5-hydroxy-5-pyridone-2-alkoxyimino compounds lacking a hydroxide group on the 1-position (N-position) or the 4,5-dihydroxybenzyloxyimino compounds, exhibit antibacterial power, especially much more excellent antibacterial activity against Gram negative microorganisms droxy-4-pyridon-2-yl) methoxyiminoacetamido]-3-pyridiniummethyl-ceph-3-em-4-carboxylate.

3. An antibacterial pharmaceutical composition containing an effective amount of a compound of claim 1 and a pharmaceutically acceptable carrier.

* * * * *